US008147965B2

(12) United States Patent
Shi et al.

(10) Patent No.: US 8,147,965 B2
(45) Date of Patent: Apr. 3, 2012

(54) WATER-SENSITIVE FILM CONTAINING THERMOPLASTIC POLYURETHANE

(75) Inventors: Bo Shi, Neenah, WI (US); James H. Wang, Appleton, WI (US); Gregory J. Wideman, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 976 days.

(21) Appl. No.: 12/120,260

(22) Filed: May 14, 2008

(65) Prior Publication Data

US 2009/0286031 A1    Nov. 19, 2009

(51) Int. Cl.
  *B32B 27/40*  (2006.01)
  *B32B 33/00*  (2006.01)
(52) U.S. Cl. .......... 428/423.1; 428/522; 428/41.5; 428/41.8; 602/58
(58) Field of Classification Search .......... 428/41.8, 428/423.1, 500, 522, 41.5; 602/58; 524/500, 524/391
See application file for complete search history.

(56) References Cited

U.S. PATENT DOCUMENTS

| | | | |
|---|---|---|---|
| 3,137,592 | A | 6/1964 | Protzman et al. |
| 3,655,129 | A | 4/1972 | Seiner |
| 3,963,656 | A | 6/1976 | Meisert et al. |
| 4,174,330 | A | 11/1979 | Gilbert et al. |
| 4,209,417 | A | 6/1980 | Whyte |

(Continued)

FOREIGN PATENT DOCUMENTS

EP    0565386 A1    10/1993

(Continued)

OTHER PUBLICATIONS

Search Report and Written Opinion for PCT/IB2009/051204 dated Oct. 29, 2009, 14 pages.

(Continued)

*Primary Examiner* — Thao T. Tran
(74) *Attorney, Agent, or Firm* — Dority & Manning, P.A.

(57) ABSTRACT

A film that contains a thermoplastic polyurethane and water-soluble polymer is provided. The film is both elastic and water-sensitive (e.g., water-soluble, water-dispersible, etc.) in that it loses its integrity over time in the presence of water. The dual attributes of elasticity and water-sensitivity may be achieved by reducing the tendency of the thermoplastic polyurethane and water-soluble polymer to form separate phases. Namely, phase separation may cause the elastomer to act as a barrier and limit the ability of the water-soluble polymer to contact water and thereby disperse. To minimize such phase separation, a variety of aspects of the film construction may be selectively controlled, such as the nature of the thermoplastic polyurethane and water-soluble polymer, the relative amount of each component, and so forth. For example, thermoplastic polyurethanes are polar in nature and thus may be generally compatible with water-soluble polymers (e.g., polyvinyl alcohol), which are also polar in nature. Further, water-soluble polymers having a relatively low molecular weight and viscosity typically possess better melt compatibility with polar thermoplastic polyurethanes. By carefully controlling the nature of the polymers used to form the film, the present inventors have discovered that a film may be formed that is generally free of distinct phases.

22 Claims, 3 Drawing Sheets

U.S. PATENT DOCUMENTS

| | | | |
|---|---|---|---|
| 4,307,219 A * | 12/1981 | Larson | 528/71 |
| 4,310,577 A * | 1/1982 | Davison et al. | 428/1.61 |
| 4,797,468 A | 1/1989 | De Vries | |
| 4,933,237 A * | 6/1990 | Krenceski et al. | 428/423.7 |
| 5,028,648 A | 7/1991 | Famili et al. | |
| 5,028,658 A | 7/1991 | David et al. | |
| 5,093,422 A | 3/1992 | Himes | |
| 5,102,465 A | 4/1992 | Lamond | |
| 5,149,591 A * | 9/1992 | Patitsas et al. | 428/423.1 |
| 5,169,706 A | 12/1992 | Collier, IV et al. | |
| 5,270,103 A * | 12/1993 | Oliver et al. | 428/219 |
| 5,292,783 A | 3/1994 | Buchanan et al. | |
| 5,367,003 A | 11/1994 | Petcavich | |
| 5,382,611 A | 1/1995 | Stepto et al. | |
| 5,397,834 A | 3/1995 | Jane et al. | |
| 5,446,079 A | 8/1995 | Buchanan et al. | |
| 5,470,944 A | 11/1995 | Bonsignore | |
| 5,523,293 A | 6/1996 | Jane et al. | |
| 5,559,171 A | 9/1996 | Buchanan et al. | |
| 5,580,911 A | 12/1996 | Buchanan et al. | |
| 5,599,858 A | 2/1997 | Buchanan et al. | |
| 5,605,961 A | 2/1997 | Lee et al. | |
| 5,639,518 A * | 6/1997 | Ando et al. | 427/544 |
| 5,641,562 A | 6/1997 | Larson et al. | |
| 5,665,152 A | 9/1997 | Bassi et al. | |
| 5,747,648 A | 5/1998 | Bassi et al. | |
| 5,770,682 A | 6/1998 | Ohara et al. | |
| 5,817,721 A | 10/1998 | Warzelhan et al. | |
| 5,821,327 A | 10/1998 | Oota et al. | |
| 5,880,254 A | 3/1999 | Ohara et al. | |
| 5,900,322 A | 5/1999 | Buchanan et al. | |
| 5,910,545 A | 6/1999 | Tsai et al. | |
| 5,922,379 A | 7/1999 | Wang | |
| 5,939,192 A | 8/1999 | Rettenbacher et al. | |
| 5,945,480 A | 8/1999 | Wang et al. | |
| 5,965,708 A | 10/1999 | Bassi et al. | |
| 5,977,312 A | 11/1999 | Bassi et al. | |
| 5,981,012 A | 11/1999 | Pomplun et al. | |
| 5,985,396 A | 11/1999 | Kerins et al. | |
| 6,008,276 A | 12/1999 | Kalbe et al. | |
| 6,020,425 A | 2/2000 | Wang et al. | |
| 6,063,866 A | 5/2000 | Wang et al. | |
| 6,075,118 A | 6/2000 | Wang et al. | |
| 6,096,809 A | 8/2000 | Lorcks et al. | |
| 6,135,987 A | 10/2000 | Tsai et al. | |
| 6,225,388 B1 | 5/2001 | Tsai et al. | |
| 6,231,970 B1 | 5/2001 | Andersen et al. | |
| 6,235,816 B1 | 5/2001 | Lorcks et al. | |
| 6,258,924 B1 | 7/2001 | Warzelhan et al. | |
| 6,296,914 B1 | 10/2001 | Kerins et al. | |
| 6,297,347 B1 | 10/2001 | Warzelhan et al. | |
| 6,326,458 B1 | 12/2001 | Gruber et al. | |
| 6,350,518 B1 | 2/2002 | Schertz et al. | |
| 6,369,215 B1 | 4/2002 | Peltonen et al. | |
| 6,414,108 B1 | 7/2002 | Warzelhan et al. | |
| 6,417,312 B1 | 7/2002 | Kirchmeyer et al. | |
| 6,469,099 B1 | 10/2002 | Farah et al. | |
| 6,517,625 B2 | 2/2003 | Bassi et al. | |
| 6,530,910 B1 | 3/2003 | Pomplun et al. | |
| 6,544,455 B1 | 4/2003 | Tsai et al. | |
| 6,552,124 B2 | 4/2003 | Wang et al. | |
| 6,552,162 B1 | 4/2003 | Wang et al. | |
| 6,565,640 B1 | 5/2003 | Bengs et al. | |
| 6,586,354 B1 | 7/2003 | Topolkaraev et al. | |
| 6,605,367 B2 | 8/2003 | Bassi et al. | |
| 6,660,211 B2 | 12/2003 | Topolkaraev et al. | |
| 6,676,984 B1 | 1/2004 | Sharp et al. | |
| 6,703,115 B2 | 3/2004 | Hale et al. | |
| 6,709,671 B2 | 3/2004 | Zerbe et al. | |
| 6,713,595 B2 | 3/2004 | Chung et al. | |
| 6,746,705 B2 | 6/2004 | Altieri et al. | |
| 6,749,795 B2 | 6/2004 | Murphy | |
| 6,767,961 B1 | 7/2004 | Wang et al. | |
| 6,806,353 B2 | 10/2004 | Zhang et al. | |
| 6,838,403 B2 | 1/2005 | Tsai et al. | |
| 6,890,989 B2 | 5/2005 | Wang et al. | |
| 6,905,759 B2 | 6/2005 | Topolkaraev et al. | |
| 6,921,581 B2 | 7/2005 | Van Gelder et al. | |
| 6,933,335 B1 | 8/2005 | Berger et al. | |
| 6,946,506 B2 | 9/2005 | Bond et al. | |
| 6,958,371 B1 | 10/2005 | Wang et al. | |
| 6,984,426 B2 | 1/2006 | Miksic et al. | |
| 6,987,138 B2 | 1/2006 | Tokiwa et al. | |
| 7,012,116 B1 | 3/2006 | Schertz et al. | |
| 7,045,650 B2 | 5/2006 | Lawrey et al. | |
| 7,053,151 B2 | 5/2006 | Wang et al. | |
| 7,098,292 B2 | 8/2006 | Zhao et al. | |
| 7,124,450 B2 | 10/2006 | Davidson | |
| 7,153,354 B2 | 12/2006 | Narayan et al. | |
| 7,153,569 B2 | 12/2006 | Kaufman et al. | |
| 7,235,594 B2 | 6/2007 | Han et al. | |
| 7,297,394 B2 | 11/2007 | Khemani et al. | |
| 7,307,125 B2 | 12/2007 | Chundury et al. | |
| 7,368,160 B2 | 5/2008 | Inglis | |
| 7,402,618 B2 | 7/2008 | Xu | |
| 7,413,731 B2 | 8/2008 | Heltovics et al. | |
| 2002/0098341 A1 | 7/2002 | Schiffer et al. | |
| 2003/0077395 A1 | 4/2003 | Bassi et al. | |
| 2003/0099692 A1 | 5/2003 | Lydzinski et al. | |
| 2003/0121101 A1 | 7/2003 | Corzani et al. | |
| 2003/0232933 A1 | 12/2003 | Lagneaux et al. | |
| 2004/0034149 A1 | 2/2004 | Garcia | |
| 2004/0059018 A1 * | 3/2004 | Gagliardi et al. | 523/111 |
| 2004/0108611 A1 | 6/2004 | Dennis et al. | |
| 2005/0186256 A1 | 8/2005 | Dihel et al. | |
| 2005/0208294 A1 | 9/2005 | Kaufman et al. | |
| 2005/0244606 A1 | 11/2005 | Egawa | |
| 2006/0135728 A1 | 6/2006 | Peerlings et al. | |
| 2006/0149199 A1 | 7/2006 | Topolkaraev et al. | |
| 2007/0031555 A1 | 2/2007 | Axelrod et al. | |
| 2007/0049685 A1 | 3/2007 | Hansel et al. | |
| 2007/0049719 A1 | 3/2007 | Brauer et al. | |
| 2007/0129467 A1 | 6/2007 | Scheer | |
| 2007/0246867 A1 | 10/2007 | Nelson et al. | |
| 2007/0298237 A1 | 12/2007 | Goino et al. | |
| 2008/0147034 A1 | 6/2008 | Wang et al. | |
| 2009/0054548 A1 | 2/2009 | Wang et al. | |

FOREIGN PATENT DOCUMENTS

| | | |
|---|---|---|
| EP | 1235879 B1 | 5/2004 |
| EP | 1075188 B1 | 11/2005 |
| WO | WO 0136535 A1 | 5/2001 |
| WO | WO 02053376 A2 | 7/2002 |
| WO | WO 02053376 A3 | 7/2002 |
| WO | WO 2005113616 A2 | 12/2005 |
| WO | WO 2005113616 A3 | 12/2005 |

OTHER PUBLICATIONS

ASTM D 1238-04c—*Standard Test Method for Melt Flow Rates of Thermoplastics by Extrusion Plastometer*, Current edition approved Dec. 1, 2004, Originally approved in 1965, pp. 1-14.

ASTM D 1343-56—*Standard Method of Test for Viscosity of Cellulose Derivatives by Ball-Drop Method*, Adopted 1956, pp. 486-489.

ASTM D 1505-03—*Standard Test Method for Density of Plastics by the Density-Gradient Technique*, Current edition approved Nov. 1, 2003, Originally approved in 1957, pp. 1-7.

ASTM D 1525-07—*Standard Test Method for Vicat Softening Temperature of Plastics*, Current edition approved Mar. 1, 2007, Originally approved in 1958, pp. 1-9.

ASTM D 3418-03 (D 3417-99)—*Standard Test Method for Transition Temperatures and Enthalpies of Fusion and Crystallization of Polymers by Differential Scanning Calorimetry*, Current edition approved Dec. 1, 2003, Originally approved in 1976, pp. 66-72.

ASTM D 3806-98 (Reapproved 2004)—*Standard Test Method of Small-Scale Evaluation of Fire-Retardant Paints (2-Foot Tunnel Method)*, Current edition approved Jun. 1, 2004, Originally approved in 1979, pp. 1-6.

ASTM D 5034-95—*Standard Test Method for Breaking Strength and Elongation of Textile Fabrics (Grab Test)*, Current edition approved May 15, 1995, pp. 674-681.

ASTM D 5338-92—*Standard Test Method for Determining Aerobic Biodegradation of Plastic Materials Under Controlled Composting Conditions*, Current edition approved Dec. 15, 1992, pp. 456-461.

ASTM D 638-08—*Standard Test Method for Tensile Properties of Plastics*, Current edition approved Apr. 1, 2008, Originally approved in 1941, pp. 1-16.

ASTM D 790-99—*Standard Test Methods for Flexural Properties of Unreinforced and Reinforced Plastics and Electrical Insulating Materials*, Current edition approved Nov. 10, 1999, pp. 150-158.

Article—*Aging Properties of Films of Plasticized Vital Wheat Gluten Cast from Acidic and Basic Solutions*, Olabarrieta et al., Biomacromolecules, vol. 7, No. 5, 2006, pp. 1657-1664.

Article—*Biodegradable Compositions by Reactive Processing of Aliphatic Polyester/Polysaccharide Blends*, Dubois et al., Macromol. Symp., vol. 198, 2003, pp. 233-243.

Article—*Biodegradable Soy Protein-Polyester Blends by Reactive Extrusion Process*, Graiver et al., Journal of Applied Polymer Science, vol. 92, 2004, pp. 3231-3239.

Article—*Chemical Modification of Starch*, Tomasik et al., Advances in Carbohydrate Chemistry and Biochemistry, vol. 59, 2004, pp. 175-316.

Article—*Edible Protein Films and Coatings*, Food Proteins and Their Applications edited by S. Damodaran and A. Paraf, John M. Krochta, 1997, pp. 529-539.

Article—*Effects of Extruder Die Nozzle Dimensions on Expansion and Micrographic Characterization During Extrusion of Acetylated Starch*, Ganjyal et al., Starch/Stärke, vol. 56, 2004, pp. 108-117.

Article—*Extrusion of Wheat Gluten Plasticized with Glycerol: Influence of Process Conditions on Flow Behavior, Rheological Properties and Molecular Size Distribution*, Redl et al., Cereal Chemistry, vol. 76, No. 3, 1999, pp. 361-370.

Article—*Glycol Glucosides from Starch by Continuous Twin-Screw Extruder Processing*, Carr et al., Cereal Chemistry, vol. 66, No. 3, 1989, pp. 238-243.

Article—*Heat and shear mediated polymerization of plasticized wheat gluten protein upon mixing*, Redl et al., Journal of Cereal Science 38, 2003, pp. 105-114.

Article—*Polyurethane/Polyolefin Blends: Morphology, Compatibilization and Mechanical Properties*, Wang et al., Polymers & Polymer Composites, vol. 14, No. 1, 2006, 11 pages.

Article—*Preparation of Acetylated Distarch Adipates by Extrusion*, Mail et al., Lebensmittel-Wissenschaft und-Technologie, vol. 34, No. 6, 2001, pp. 384-389.

Article—*Reactivity of Wheat Gluten Protein during Mechanical Mixing: Radical and Nucleophilic Reactions for the Addition of Molecules on Sulfur*, Auvergne et al., Biomacromolecules, vol. 9, No. 2, 2008, pp. 664-671.

Article—*Soy Protein-Based Biodegradable Plastics*, Mungara et al., Proceedings in Plastics Impact on the Environment Conference, Society of Plastic, Feb. 2003, pp. 393-397.

Article—*Starch Modification, Destruction and Hydrolysis during O-Formylation*, Divers et al., Starch/Stärke 56, 2004, pp. 389-398.

Article—*The chemical modification of a range of starches under aqueous reaction conditions*, Fang et al., Carbohydrate Polymers 55, 2004, pp. 283-289.

Article—*The History of Tomorrow's Materials: Protein-Based Biopolymers*, Ralston et al., Plastics Engineering, Feb. 2008, pp. 36-40.

Article—*The Hydroxypropylation of Starch in a Self-Wiping Twin Screw Extruder*, De Graaf et al., Advances in Polymer Technology, vol. 22, No. 1, 2003, pp. 56-68.

Article—*Thermoplastic Processing of Protein-Based Bioplastics: Chemical Engineering Aspects of Mixing, Extrusion and Hot Molding*, Pommet et al., Macromol. Symp., vol. 197, 2003, pp. 207-217.

Article—*Thermoplastic Processing of Proteins for Film Formation—A Review*, Hernandez-Izquierdo et al., Journal of Food Science, vol. 73, No. 2, 2008, pp. R30-R39.

Related U.S. Patent Applications.

\* cited by examiner

WATER-SENSITIVE FILM CONTAINING THERMOPLASTIC POLYURETHANE

BACKGROUND OF THE INVENTION

Films are employed in a wide variety of disposable goods, such as diapers, sanitary napkins, adult incontinence garments, bandages, etc. For example, many sanitary napkins have an adhesive strip on the backside of the napkin (the napkin surface opposite to the body-contacting surface) to affix the napkin to an undergarment and hold the napkin in place against the body. Before use, the adhesive strip is protected with a peelable release liner. Once removed, the peelable release liner must be discarded. Conventional release liners may contain a film or paper coated with a release coating. Such release-coated films or papers, however, do not readily disperse in water, and as such, disposal options are limited to depositing the release liner in a trash receptacle. Although disposing of conventional release liners in a toilet would be convenient to the consumer, it would potentially create blockages in the toilet.

Flushable films have been developed that are formed from a water-dispersible polymer. U.S. Pat. No. 6,296,914 to Kerins, et al. describes a water-sensitive film that may include, for instance, polyethylene oxide, ethylene oxide-propylene oxide copolymers, polymethacrylic acid, polymethacrylic acid copolymers, polyvinyl alcohol, poly(2-ethyl oxazoline), polyvinyl methyl ether, polyvinyl pyrrolidone/vinyl acetate copolymers, methyl cellulose, ethyl cellulose, hydroxypropyl cellulose, hydroxypropyl methyl cellulose, ethyl hydroxyethyl cellulose, methyl ether starch, poly (n-isopropyl acrylamide), poly N-vinyl caprolactam, polyvinyl methyl oxazolidone, poly (2-isopropyl-2-oxazoline), poly (2,4-dimethyl-6-triazinyl ethylene), or a combination thereof. Some of these polymers, however, are not thermoplastic and thus are not readily processed using thermoplastic film converting equipment. Further, these films are also not elastic and may thus be limited in their use. In response to these and other problems, attempts have been made to form water-shrinkable films from elastomeric and water-dispersible polymers. One such film is described in U.S. Pat. No. 5,641,562 to Larson, et al. In one example, the film is formed that contains polyethylene oxide having a molecular weight of about 200,000 and an ethylene vinyl acetate copolymer. Although such films are shrinkable, they nevertheless are not dispersible or disintegratable in water so as to achieve complete flushability. Furthermore the films are not elastic.

As such, a need currently exists for an improved film that is both elastic and water-sensitive in that it readily loses its integrity over time in the presence of water.

SUMMARY OF THE INVENTION

In accordance with one embodiment of the present invention, a water-sensitive elastic film is disclosed that comprises at least one water-soluble polymer, at least one plasticizer, and at least one thermoplastic polyurethane synthesized from at least one polyol and at least one organic diisocyanate. The water-soluble polymer has a weight average molecular weight of from about 10,000 to about 150,000 grams per mole and a number average molecular weight of from about 1,000 to about 80,000 grams per mole. The weight ratio of the water-soluble polymer to the plasticizer is from about 1 to about 50 and the weight ratio of the water-soluble polymer to the thermoplastic polyurethane is from about 0.01 to about 3.0.

In accordance with another embodiment of the present invention, a method for forming a water-sensitive, elastic film is disclosed. The method comprises melt blending a composition that comprises at least one water-soluble polymer, at least one plasticizer, and at least one thermoplastic polyurethane synthesized from at least one polyol and at least one organic diisocyanate. The method also comprises extruding the composition to form a film.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which.

Figure 1:
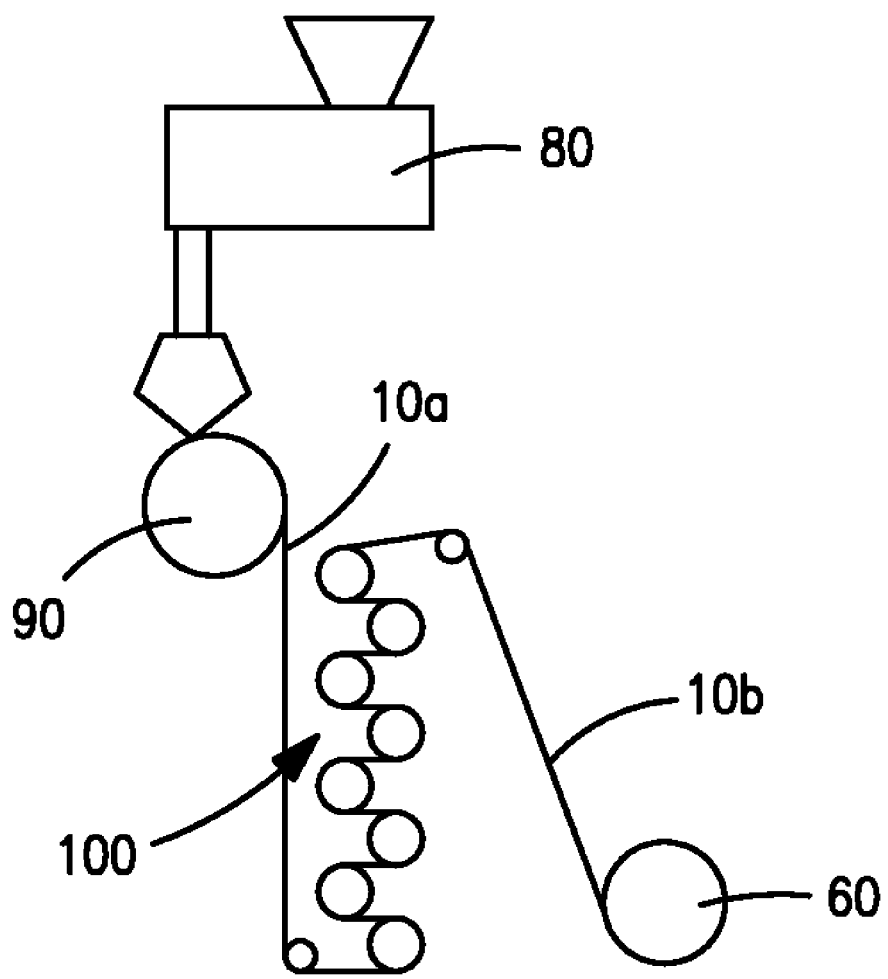
FIG. 1 is a schematic illustration of one embodiment of a method for forming a film in accordance with the present invention.

Repeat use of references characters in the present specification and drawings is intended to represent same or analogous features or elements of the invention.

DETAILED DESCRIPTION OF REPRESENTATIVE EMBODIMENTS

Definitions

As used herein, the terms "machine direction" or "MD" generally refers to the direction in which a material is produced. The term "cross-machine direction" or "CD" refers to the direction perpendicular to the machine direction. Dimensions measured in the cross-machine direction are referred to as "width" dimension, while dimensions measured in the machine direction are referred to as "length" dimensions.

As used herein, the term "elastomeric" and "elastic" and refers to a material that, upon application of a stretching force, is stretchable in at least one direction (such as the CD direction), and which upon release of the stretching force, contracts/returns to approximately its original dimension. For example, a stretched material may have a stretched length that is at least 50% greater than its relaxed unstretched length, and which will recover to within at least 50% of its stretched length upon release of the stretching force. A hypothetical example would be a one (1) inch sample of a material that is stretchable to at least 1.50 inches and which, upon release of the stretching force, will recover to a length of at least 1.25 inches. Desirably, the material contracts or recovers at least 50%, and even more desirably, at least 80% of the stretched length.

As used herein the terms "extensible" or "extensibility" generally refers to a material that stretches or extends in the direction of an applied force by at least about 50% of its relaxed length or width. An extensible material does not necessarily have recovery properties. For example, an elastomeric material is an extensible material having recovery properties. A film may be extensible, but not have recovery properties, and thus, be an extensible, non-elastic material.

As used herein, the term "percent stretch" refers to the degree to which a material stretches in a given direction when subjected to a certain force. In particular, percent stretch is determined by measuring the increase in length of the material in the stretched dimension, dividing that value by the original dimension of the material, and then multiplying by 100.

As used herein, the term "set" refers to retained elongation in a material sample following the elongation and recovery, i.e., after the material has been stretched and allowed to relax during a cycle test.

As used herein, the term "percent set" is the measure of the amount of the material stretched from its original length after being stretched and relaxed. The remaining strain after the removal of the applied stress is measured as the percent set.

Detailed Description

Reference now will be made in detail to various embodiments of the invention, one or more examples of which are set forth below. Each example is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. Thus, it is intended that the present invention covers such modifications and variations as come within the scope of the appended claims and their equivalents.

Generally speaking, the present invention is directed to a film that contains a thermoplastic polyurethane and water-soluble polymer. The film is both elastic and water-sensitive (e.g., water-soluble, water-dispersible, etc.) in that it loses its integrity over time in the presence of water. The dual attributes of elasticity and water-sensitivity may be achieved by reducing the tendency of the thermoplastic polyurethane and water-soluble polymer to form separate phases. Namely, phase separation may cause the elastomer to act as a barrier and limit the ability of the water-soluble polymer to contact water and thereby disperse. To minimize such phase separation, a variety of aspects of the film construction may be selectively controlled, such as the nature of the thermoplastic polyurethane and water-soluble polymer, the relative amount of each component, and so forth. For example, thermoplastic polyurethanes are polar in nature and thus may be generally compatible with water-soluble polymers (e.g., polyvinyl alcohol), which are also polar in nature. Further, water-soluble polymers having a relatively low molecular weight and viscosity typically possess better melt compatibility with polar thermoplastic polyurethanes. By carefully controlling the nature of the polymers used to form the film, the present inventors have discovered that a film may be formed that is generally free of distinct phases.

In this regard, various embodiments of the present invention will now be described in more detail below.
I. Film Components
 A. Thermoplastic Polyurethane
  Thermoplastic polyurethanes are generally synthesized from a polyol, organic diisocyanate, and optionally a chain extender. The synthesis of such melt-processable polyurethane elastomers may proceed either stepwise (e.g., prepolymer dispensing process) or by simultaneous reaction of all components in a single stage (e.g., one-shot dispensing process) as is known in the art and described in more detail in U.S. Pat. No. 3,963,656 to Meisert, et al.; U.S. Pat. No. 5,605,961 to Lee, et al.; U.S. Pat. No. 6,008,276 to Kalbe, et al.; U.S. Pat. No. 6,417,312 to Kirchmeyer, et al.; and U.S. Pat. No. 7,045,650 to Lawrey, et al., as well as U.S. Patent Application Publication Nos. 2006/0135728 to Peerlinqs, et al. and 2007/0049719 to Brauer, et al., all of which are incorporated herein in their entirety by reference thereto for all purposes.

A polyol is generally any high molecular weight product having an active hydrogen component that may be reacted and includes materials having an average of about two or more hydroxyl groups per molecule. Long-chain polyols may be used that include higher polymeric polyols, such as polyester polyols and polyether polyols, as well as other acceptable "polyol" reactants, which have an active hydrogen component such as polyester polyols, polyhydroxy polyester amides, hydroxyl containing polycaprolactones, hydroxy-containing acrylic interpolymers, hydroxy-containing epoxies, and hydrophobic polyalkylene ether polyols. Typically, the polyol is substantially linear and has two to three, and more preferably two hydroxyl groups, and a number average molecular weight of from about 450 to about 10,000, in some embodiments from about 450 to about 6000, and in some embodiments from about 600 to about 4500. Suitable polyether diols may be produced by, for example, reacting one or more alkylene oxides having 2 to 4 carbon atoms in the alkylene residue with a starter molecule that contains two or more active hydrogen atoms in bound form. Exemplary alkylene oxides include ethylene oxide, 1,2-propylene oxide, epichlorohydrin and 1,2-butylene oxide and 2,3-butylene oxide. Exemplary starter molecules include water; aminoalcohols, such as N-alkyl-diethanolamines (e.g., N-methyl-diethanolamine); and diols, such as ethylene glycol, 1,3-propylene glycol, 1,4-butanediol and 1,6-hexanediol. Suitable polyester diols may be produced from dicarboxylic acids (or derivatives thereof) having 2 to 12 carbon atoms, preferably 4 to 6 carbon atoms, and polyhydric alcohols. Exemplary dicarboxylic acids include aliphatic dicarboxylic acids, such as succinic acid, glutaric acid, adipic acid, suberic acid, azelaic acid and sebacic acid; aromatic dicarboxylic acids, such as phthalic acid, isophthalic acid and terephthalic acid; as well as derivatives of such acids, such as carboxylic acid diesters having 1 to 4 carbon atoms in the alcohol residue, carboxylic anhydrides or carboxylic acid chlorides. Examples of suitable polyhydric alcohols include glycols with 2 to 10, preferably 2 to 6 carbon atoms, such as ethylene glycol, diethylene glycol, 1,4-butanediol, 1,5-pentanediol, 1,6-hexanediol, 1,10-decanediol, 2,2-dimethyl-1,3-propanediol, 1,3-propanediol, and dipropylene glycol. Esters of carbonic acid with the stated diols are also suitable, and particularly, those having 4 to 6 carbon atoms, such as 1,4-butanediol or 1,6-hexanediol; condensation products of ω-hydroxycarboxylic acids, such as ω-hydroxycaproic acid or polymerisation products of lactones (e.g., optionally substituted ω-caprolactones). Preferred polyester diols include ethanediol polyadipates, 1,4-butanediol polyadipates, ethanediol/1,4-butanediol polyadipates, 1,6-hexanediol/neopentyl glycolpolyadipates, 1,6-hexanediol/1,4-butanediol polyadipates and polycaproplactones.

The organic diisocyanates may include aliphatic diisocyanates, such as ethylene diisocyanate, 1,4-tetramethylene diisocyanate, 1,12-dodecane diisocyanate, 1,6-hexamethylene diisocyanate, mixtures thereof, etc.; cycloaliphatic diisocyanates, such as isophorone diisocyanate, 1,4-cyclohexane diisocyanate, 1-methyl-2,4-cyclohexane diisocyanate, 1-methyl-2,6-cyclohexane diisocyanate, 4,4'-,2,4'- or 2,2'-dicyclohexylmethane diisocyanate, mixtures thereof, etc.; and/or aromatic diisocyanates, such as 2,4- or 2,6-toluene diisocyanate, 4,4'-diphenylmethane diisocyanate, 2,4'-diphenylmethane diisocyanate, 2,2'-diphenylmethane diisocyanate, naphthylene-1,5-diisocyanate, xylylene diisocyanate, methylene diphenyl isocyanate ("MDI"), hexamethylene diisocyanate ("HMDI"), mixtures thereof, etc.

The chain extenders typically have a number average molecular weight of from about 60 to about 400 and contains amino, thiol, carboxyl, and/or hydroxyl functional groups. The preferred chain extenders are those having two to three, and more preferably two, hydroxyl groups. As set forth above, one or more compounds selected from the aliphatic diols that contain from 2 to 14 carbon atoms may be used as the chain extender. Such compounds include, for example, ethanediol, 1,2-propanediol, 1,3-propanediol, 1,4-butanediol, 2,3-butanediol, 1,5-pentanediol, 1,6-hexanediol, diethylene glycol, dipropylene glycol, 1,4-cyclohexanediol, 1,4-dimethanolcyclohexane and neopentyl glycol. Diesters of terephthalic acid with glycols having 2 to 4 carbon atoms may also be employed. Some examples of such compounds include terephthalic acid bis-ethylene glycol and terephthalic acid bis-1,4-butanediol, hydroxyalkylene ethers of hydroquinone (e.g., 1-4-di(β-hydroxyethyl)hydroquinone), ethoxylated bisphenols (e.g., 1,4-di(β-hydroxyethyl)bisphenol A), (cyclo)aliphatic diamines (e.g., isophoronediamine, ethylendiamine, 1,2-propylenediamine, 1,3-propylenediamine, N-methyl-1,3-propylenediamine, and N,N'-dimethylethylenediamine), and aromatic diamines (e.g., 2,4-toluenediamine, 2,6-toluenediamine, 3,5-diethyl-2,4-toluenediamine and 3,5-diethyl-2,6-toluenediamine, and primary mono-, di-, tri- or tetraalkyl-substituted 4,4'-diaminodiphenylmethanes).

In addition to those noted above, other components may also be employed to form the thermoplastic polyurethane. Catalysts, for instance, may be employed to facilitate formation of the polyurethane. Suitable catalysts include, for instance, tertiary amines, such as triethylamine, dimethylcyclohexyl-amine, N-methylmorpholine, N, N'-dimethylpiperazine, 2-(dimethylaminoethoxy)-ethanol, diazabicyclo [2.2.2]octane, etc. as well as metal compounds, such as titanic acid esters, tin diacetate, tin dioctoate, tin dilaurate or the dialkyltin salts of aliphatic carboxylic acids such as dibutyltin diacetate or dibutyltin dilaurate or other similar compounds. Still other suitable additives that may be employed include light stablizers (e.g., hindered amines), chain terminators, slip agents and mold release agents (e.g., fatty acid esters, the metal soaps thereof, fatty acid amides, fatty acid ester amides and silicone compounds), plasticizers, antiblocking agents, inhibitors, stabilizers against hydrolysis, heat and discoloration, dyes, pigments, inorganic and/or organic fillers, fungistatically and bacteriostatically active substances, fillers, etc.

The thermoplastic polyurethane typically has a melting point of from about 75° C. to about 250° C., in some embodiments from about 100° C. to about 240° C., and in some embodiments, from about 120° C. to about 220° C. The glass transition temperature ("$T_g$") of the thermoplastic polyurethane may be relatively low, such as from about −150° C. to about 0° C., in some embodiments from about −100° C. to about −10° C., and in some embodiments, from about −85° C. to about −20° C. The melting temperature and glass transition temperature may be determined using differential scanning calorimetry ("DSC") in accordance with ASTM D-3417. Examples of such thermoplastic polyurethanes are available under the designation DESMOPAN™ from Bayer MaterialScience and under the designation ESTANE™ from Lubrizol. DESMOPAN™ DP 9370A, for instance, is an aromatic polyether-based polyurethane formed from poly(tetramethylene ether glycol) and 4,4-methylenebis(phenylisocyanate) ("MDI") and has a glass transition temperature of about −70° C. and a melting temperature of from about 188° C. to about 199° C. ESTANE™ 58245 is likewise an aromatic polyetherbased polyurethane having a glass transition temperature of about −37° C. and a melting temperature of from about 135° C. to about 159° C.

B. Water-Soluble Polymer

The film also includes one or more water-soluble polymers. Such polymers may be formed from monomers such as vinyl pyrrolidone, hydroxyethyl acrylate or methacrylate (e.g., 2-hydroxyethyl methacrylate), hydroxypropyl acrylate or methacrylate, acrylic or methacrylic acid, acrylic or methacrylic esters or vinyl pyridine, acrylamide, vinyl acetate, vinyl alcohol (hydrolyzed from vinyl acetate), ethylene oxide, derivatives thereof, and so forth. Other examples of suitable monomers are described in U.S. Pat. Nos. 4,499,154 to James, et al., which is incorporated herein in its entirety by reference thereto for all purposes. The resulting polymers may be homopolymers or interpolymers (e.g., copolymer, terpolymer, etc.), and may be nonionic, anionic, cationic, or amphoteric. In addition, the polymer may be of one type (i.e., homogeneous), or mixtures of different polymers may be used (i.e., heterogeneous). In one particular embodiment, the water-soluble polymer contains a repeating unit having a functional hydroxyl group, such as polyvinyl alcohol ("PVOH"), copolymers of polyvinyl alcohol (e.g., ethylene vinyl alcohol copolymers, methyl methacrylate vinyl alcohol copolymers, etc.), etc. Vinyl alcohol polymers, for instance, have at least two or more vinyl alcohol units in the molecule and may be a homopolymer of vinyl alcohol, or a copolymer containing other monomer units. Vinyl alcohol homopolymers may be obtained by hydrolysis of a vinyl ester polymer, such as vinyl formate, vinyl acetate, vinyl propionate, etc. Vinyl alcohol copolymers may be obtained by hydrolysis of a copolymer of a vinyl ester with an olefin having 2 to 30 carbon atoms, such as ethylene, propylene, 1-butene, etc.; an unsaturated carboxylic acid having 3 to 30 carbon atoms, such as acrylic acid, methacrylic acid, crotonic acid, maleic acid, fumaric acid, etc., or an ester, salt, anhydride or amide thereof; an unsaturated nitrile having 3 to 30 carbon atoms, such as acrylonitrile, methacrylonitrile, etc.; a vinyl ether having 3 to 30 carbon atoms, such as methyl vinyl ether, ethyl vinyl ether, etc.; and so forth.

The degree of hydrolysis may be selected to optimize solubility, etc., of the polymer. For example, the degree of hydrolysis may be from about 60 mole % to about 95 mole %, in some embodiments from about 80 mole % to about 90 mole %, and in some embodiments, from about 85 mole % to about 89 mole %. Examples of suitable partially hydrolyzed polyvinyl alcohol polymers are available under the designation CELVOL™ 203, 205, 502, 504, 508, 513, 518, 523, 530, or 540 from Celanese Corp. Other suitable partially hydrolyzed polyvinyl alcohol polymers are available under the designation ELVANOL™ 50-14, 50-26, 50-42, 51-03, 51-04, 51-05, 51-08, and 52-22 from DuPont.

The water-soluble polymers employed in the present invention generally have a low molecular weight. For example, the water-soluble polymers may have a number average molecular weight ("$M_n$") ranging from about 1,000 to about 80,000 grams per mole, in some embodiments from about 5,000 to about 60,000 grams per mole, and in some embodiments, from about 10,000 to about 40,000 grams per mole. Likewise, the water-soluble polymers may also have a weight average molecular weight ("$M_w$") ranging from about 10,000 to about 150,000 grams per mole, in some embodiments from about 20,000 to about 100,000 grams per mole, and in some embodiments, from about 30,000 to about 75,000 grams per mole. The ratio of the weight average molecular weight to the number average molecular weight ("$M_w/M_n$"), i.e., the "polydispersity index", is also relatively low. For example, the polydispersity index typically ranges from about 1.0 to about 4.0, in some embodiments from about 1.1 to about 3.0, and in some embodiments, from about 1.2 to about 2.5. The water-soluble polymers may also have a solution viscosity of from about 50 to about 800 millipascal seconds (mPa·s), in some embodiments from about 100 to about 700 mPa·s, and in some embodiments, from about 200 to about 600 mPa·s. The solution viscosity is measured as a 4 percent aqueous solution at 20° C. by the Hoeppler falling ball method in accordance with ASTM-D 1343-56 Part 8, 1958, page 486.

A plasticizer is also employed in the present invention to help render the water-soluble polymer melt-processable. Suitable plasticizers may include, for instance, polyhydric alcohol plasticizers, such as sugars (e.g., glucose, sucrose, fructose, raffinose, maltodextrose, galactose, xylose, maltose, lactose, mannose, and erythrose), sugar alcohols (e.g., erythritol, xylitol, malitol, mannitol, and sorbitol), polyols (e.g., ethylene glycol, glycerol, propylene glycol, dipropylene glycol, butylene glycol, and hexane triol), etc. Also suitable are hydrogen bond forming organic compounds which do not have hydroxyl group, including urea and urea derivatives; anhydrides of sugar alcohols such as sorbitan; animal proteins such as gelatin; vegetable proteins such as sunflower protein, soybean proteins, cotton seed proteins; and mixtures thereof. Other suitable plasticizers may include phthalate esters, dimethyl and diethylsuccinate and related esters, glycerol triacetate, glycerol mono and diacetates, glycerol mono, di, and tripropionates, butanoates, stearates, lactic acid esters, citric acid esters, adipic acid esters, stearic acid esters, oleic acid esters, and other acid esters. Aliphatic acids may also be used, such as copolymers of ethylene and acrylic acid, polyethylene grafted with maleic acid, polybutadiene-co-acrylic acid, polybutadiene-co-maleic acid, polypropylene-co-acrylic acid, polypropylene-co-maleic acid, and other hydrocarbon based acids. A low molecular weight plasticizer is preferred, such as less than about 20,000 g/mol, preferably less than about 5,000 g/mol and more preferably less than about 1,000 g/mol.

Typically, the weight ratio of the water-soluble polymer to the plasticizer may be from about 1 to about 50, in some embodiments from about 2 to about 25, and in some embodiments, from about 3 to about 15. For example, a blend of plasticizer and water-soluble polymer ("plasticized water-soluble polymer") may contain from about 1 wt. % to about 40 wt. %, in some embodiments from about 2 wt. % to about 30 wt. %, and in some embodiments, from about 5 wt. % to about 25 wt. % of the plasticizer, and also from about 60 wt. % to about 99 wt. %, in some embodiments from about 70 wt. % to about 98 wt. %, and in some embodiments, from about 75 wt. % to about 95 wt. % of the water-soluble polymer.

Through selective control over the nature of the water-soluble polymer (e.g., molecular weight, viscosity, etc.), the nature of the plasticizer, and the relative amounts of the water-soluble polymer and plasticizer, the resulting plasticized water-soluble polymer may achieve a melt viscosity that is similar to that of the thermoplastic polyurethane, which further helps minimize phase separation during formation of the film. That is, the ratio of the melt viscosity of the thermoplastic polyurethane to the plasticized water-soluble polymer is typically from about 0.01 to about 2.0, in some embodiments from about 0.1 to about 1.75, and in some embodiments, from about 0.5 to about 1.5. For example, the plasticized water-soluble polymer may have an apparent melt viscosity of from about 10 to about 400 Pascal seconds (Pa·s), in some embodiments from about 20 to about 200 Pa·s, and in some embodiments, from about 30 to about 80 Pa·s, as determined at a temperature of 195° C. and a shear rate of 1000 sec$^{-1}$. Likewise, the apparent melt viscosity of the thermoplastic polyurethane may range from about 20 to about 500 Pascal seconds (Pa·s), in some embodiments from about 30 to about 200 Pa·s, and in some embodiments, from about 40 to about 100 Pa·s, as determined at a temperature of 195° C. and a shear rate of 1000 sect$^1$.

The relative amount of the water-soluble polymer and thermoplastic polyurethane employed in the film may also be selected to help further minimize phase separation. For example, the weight ratio of the water-soluble polymer to the thermoplastic polyurethane is typically from about 0.01 to about 3.0, in some embodiments from about 0.1 to about 2.5, and in some embodiments, from about 1.0 to about 2.0. The thermoplastic polyurethane may constitute from about 10 wt. % to about 70 wt. %, in some embodiments from about 15 wt. % to about 60 wt. %, and in some embodiments, from about 20 wt. % to about 50 wt. % of the film. The water-soluble polymer may constitute from about 20 wt. % to about 90 wt. %, in some embodiments from about 30 wt. % to about 80 wt. %, and in some embodiments, from about 40 wt. % to about 70 wt. % of the film. Likewise, the plasticizer may constitute from about 1 wt. % to about 30 wt. %, in some embodiments from about 2 wt. % to about 20 wt. %, and in some embodiments, from about 5 wt. % to about 15 wt. % of the film.

C. Other Components

Other components may also be incorporated into the film as is known in the art. In one embodiment, for example, the film may include a starch. Although starch is produced in many plants, typical sources includes seeds of cereal grains, such as corn, waxy corn, wheat, sorghum, rice, and waxy rice; tubers, such as potatoes; roots, such as tapioca (i.e., cassava and manioc), sweet potato, and arrowroot; and the pith of the sago palm. Broadly speaking, native (unmodified) and/or modified starches may be employed. Modified starches, for instance, may be employed that have been chemically modified by typical processes known in the art (e.g., esterification, etherification, oxidation, enzymatic hydrolysis, etc.). Starch ethers and/or esters may be particularly desirable, such as hydroxyalkyl starches, carboxymethyl starches, etc. The hydroxyalkyl group of hydroxylalkyl starches may contain, for instance, 2 to 10 carbon atoms, in some embodiments from 2 to 6 carbon atoms, and in some embodiments, from 2 to 4 carbon atoms. Representative hydroxyalkyl starches such as hydroxyethyl starch, hydroxypropyl starch, hydroxybutyl starch, and derivatives thereof. Starch esters, for instance, may be prepared using a wide variety of anhydrides (e.g., acetic, propionic, butyric, and so forth), organic acids, acid chlorides, or other esterification reagents. The degree of esterification may vary as desired, such as from 1 to 3 ester groups per glucosidic unit of the starch.

Further, the film may also contain one or more biodegradable polyesters. The term "biodegradable" generally refers to a material that degrades from the action of naturally occurring microorganisms, such as bacteria, fungi, and algae; environmental heat; moisture; or other environmental factors, such as determined according to ASTM Test Method 5338.92. Examples of suitable biodegradable polyesters include aliphatic polyesters, such as polycaprolactone, polyesteramides, modified polyethylene terephthalate, polylactic acid (PLA) and its copolymers, terpolymers based on polylactic acid, polyglycolic acid, polyalkylene carbonates (such as polyethylene carbonate), polyhydroxyalkanoates (PHA), poly-3-hydroxybutyrate (PHB), poly-3-hydroxyvalerate (PHV), poly-3-hydroxybutyrate-co-4-hydroybutyrate, poly-3-hydroxybutyrate-co-3-hydroxyvalerate copolymers (PHBV), poly-3-hydroxybutyrate-co-3-hydroxyhexanoate, poly-3-hydroxybutyrate-co-3-hydroxyoctanoate, poly-3-hydroxybutyrate-co-3-hydroxydecanoate, poly-3-hydroxybutyrate-co-3-hydroxyoctadecanoate, and succinate-based aliphatic polymers (e.g., polybutylene succinate, polybutylene succinate adipate, polyethylene succinate, etc.); aromatic polyesters and modified aromatic polyesters; and aliphatic-aromatic copolyesters. For example, the biodegradable polyester may be an aliphatic-aromatic copolyester having the following structure:

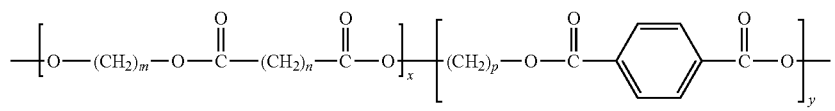

wherein, m is an integer from 2 to 10, in some embodiments from 2 to 4, and in one embodiment, 4;

n is an integer from 0 to 18, in some embodiments from 2 to 4, and in one embodiment, 4;

p is an integer from 2 to 10, in some embodiments from 2 to 4, and in one embodiment, 4;

x is an integer greater than 1; and y is an integer greater than 1. One example of such a copolyester is polybutylene adipate terephthalate, which is commercially available under the designation ECOFLEX® F BX 7011 from BASF Corp. Another example of a suitable copolyester containing an aromatic terephtalic acid monomer constituent is available under the designation ENPOL™ 8060M from IRE Chemicals (South Korea). Other suitable aliphatic-aromatic copolyesters may be described in U.S. Pat. Nos. 5,292,783; 5,446,079; 5,559,171; 5,580,911; 5,599,858; 5,817,721; 5,900,322; and 6,258,924, which are incorporated herein in their entirety by reference thereto for all purposes.

In addition to the components noted above, other additives may also be incorporated into the film of the present invention, such as slip additives (e.g., fatty acid salts, fatty acid amides, etc.), compatibilizers (e.g., functionalized polyolefins), dispersion aids, melt stabilizers, processing stabilizers, heat stabilizers, light stabilizers, antioxidants, heat aging stabilizers, whitening agents, antiblocking agents, bonding agents, lubricants, fillers, etc. Dispersion aids, for instance, may also be employed to help create a uniform dispersion of the starch/polyvinyl alcohol/plasticizer mixture and retard or prevent separation into constituent phases. Likewise, the dispersion aids may also improve the water dispersibility of the film. When employed, the dispersion aid(s) typically constitute from about 0.01 wt. % to about 15 wt. %, in some embodiments from about 0.1 wt. % to about 10 wt. %, and in some embodiments, from about 0.5 wt. % to about 5 wt. % of the film. Although any dispersion aid may generally be employed in the present invention, surfactants having a certain hydrophilic/lipophilic balance ("HLB") may improve the long-term stability of the composition. The HLB index is well known in the art and is a scale that measures the balance between the hydrophilic and lipophilic solution tendencies of a compound. The HLB scale ranges from 1 to approximately 50, with the lower numbers representing highly lipophilic tendencies and the higher numbers representing highly hydrophilic tendencies. In some embodiments of the present invention, the HLB value of the surfactants is from about 1 to about 20, in some embodiments from about 1 to about 15 and in some embodiments, from about 2 to about 10. If desired, two or more surfactants may be employed that have HLB values either below or above the desired value, but together have an average HLB value within the desired range.

One particularly suitable class of surfactants for use in the present invention are nonionic surfactants, which typically have a hydrophobic base (e.g., long chain alkyl group or an alkylated aryl group) and a hydrophilic chain (e.g., chain containing ethoxy and/or propoxy moieties). For instance, some suitable nonionic surfactants that may be used include, but are not limited to, ethoxylated alkylphenols, ethoxylated and propoxylated fatty alcohols, polyethylene glycol ethers of methyl glucose, polyethylene glycol ethers of sorbitol, ethylene oxide-propylene oxide block copolymers, ethoxylated esters of fatty ($C_8$-$C_{18}$) acids, condensation products of ethylene oxide with long chain amines or amides, condensation products of ethylene oxide with alcohols, fatty acid esters, monoglyceride or diglycerides of long chain alcohols, and mixtures thereof. In one particular embodiment, the nonionic surfactant may be a fatty acid ester, such as a sucrose fatty acid ester, glycerol fatty acid ester, propylene glycol fatty acid ester, sorbitan fatty acid ester, pentaerythritol fatty acid ester, sorbitol fatty acid ester, and so forth. The fatty acid used to form such esters may be saturated or unsaturated, substituted or unsubstituted, and may contain from 6 to 22 carbon atoms, in some embodiments from 8 to 18 carbon atoms, and in some embodiments, from 12 to 14 carbon atoms. In one particular embodiment, mono- and di-glycerides of fatty acids may be employed in the present invention.

Fillers may also be employed in the present invention. Fillers are particulates or other forms of material that may be added to the film polymer extrusion blend and that will not chemically interfere with the extruded film, but which may be uniformly dispersed throughout the film. Fillers may serve a variety of purposes, including enhancing film opacity and/or breathability (i.e., vapor-permeable and substantially liquid-impermeable). For instance, filled films may be made breathable by stretching, which causes the polymer to break away from the filler and create microporous passageways. Breathable microporous elastic films are described, for example, in U.S. Pat. Nos. 5,997,981; 6,015,764; and 6,111,163 to McCormack, et al.; U.S. Pat. No. 5,932,497 to Morman, et al.; U.S. Pat. No. 6,461,457 to Taylor, et al., which are incorporated herein in their entirety by reference thereto for all purposes. Further, hindered phenols are commonly used as an antioxidant in the production of films. Some suitable hindered phenols include those available from Ciba Specialty Chemicals under the trade name "Irganox®", such as Irganox® 1076, 1010, or E 201. Moreover, bonding agents may also be added to the film to facilitate bonding of the film to additional materials (e.g., nonwoven webs). Examples of such bonding agents include hydrogenated hydrocarbon resins. Other suitable bonding agents are described in U.S. Pat. Nos. 4,789,699 to Kieffer et al. and U.S. Pat. No. 5,695,868 to McCormack, which are incorporated herein in their entirety by reference thereto for all purposes.

II. Film Construction

The film of the present invention may be mono- or multi-layered. Multilayer films may be prepared by co-extrusion of the layers, extrusion coating, or by any conventional layering process. Such multilayer films normally contain at least one base layer and at least one skin layer, but may contain any number of layers desired. For example, the multilayer film may be formed from a base layer and one or more skin layers, wherein the base layer is formed from a blend of the water-soluble polymer and thermoplastic urethane. In most embodiments, the skin layer(s) are also formed from the blend as described above. It should be understood, however, that other polymers may also be employed in the skin layer(s).

Any known technique may be used to form a film from the compounded material, including blowing, casting, flat die extruding, etc. In one particular embodiment, the film may be formed by a blown process in which a gas (e.g., air) is used to expand a bubble of the extruded polymer blend through an annular die. The bubble is then collapsed and collected in flat film form. Processes for producing blown films are described, for instance, in U.S. Pat. No. 3,354,506 to Raley; U.S. Pat. No. 3,650,649 to Schippers; and U.S. Pat. No. 3,801,429 to Schrenk et al., as well as U.S. Patent Application Publication Nos. 2005/0245162 to McCormack, et al. and 2003/0068951 to Boggs, et al., all of which are incorporated herein in their entirety by reference thereto for all purposes. In yet another embodiment, however, the film is formed using a casting technique.

Referring to FIG. 1, for instance, one embodiment of a method for forming a cast film is shown. The raw materials (e.g., plasticizer, water-soluble polymer, thermoplastic polyurethane, etc.) may be supplied to a melt blending device, either separately or as a blend. In one embodiment, for example, the components are separately supplied to a melt blending device where they are dispersively blended in a manner such as described above. For example, an extruder may be employed that includes feeding and venting ports. In one embodiment, the thermoplastic polyurethane may be fed to a feeding port of the twin-screw extruder and melted. Thereafter, the plasticizer and water-soluble polymer may be fed into the polymer melt. Regardless, the materials are blended under high shear/pressure and heat to ensure sufficient mixing. For example, melt blending may occur at a temperature of from about 75° C. to about 400° C., in some embodiments, from about 80° C. to about 300° C., and in some embodiments, from about 90° C. to about 250° C. Likewise, the apparent shear rate during melt blending may range from about 100 seconds$^{-1}$ to about 10,000 seconds$^{-1}$, in some embodiments from about 500 seconds$^{-1}$ to about 5000 seconds$^{-1}$, and in some embodiments, from about 800 seconds$^{-1}$ to about 1200 seconds$^{-1}$. The apparent shear rate is equal to $4Q/\pi R^3$, where Q is the volumetric flow rate ("m$^3$/s") of the polymer melt and R is the radius ("m") of the capillary (e.g., extruder die) through which the melted polymer flows.

Thereafter, the extruded material may be immediately chilled and cut into pellet form. In the particular embodiment of FIG. 1, the compounded material (not shown) is then supplied to an extrusion apparatus 80 and cast onto a casting roll 90 to form a single-layered precursor film 10a. If a multilayered film is to be produced, the multiple layers are co-extruded together onto the casting roll 90. The casting roll 90 may optionally be provided with embossing elements to impart a pattern to the film. Typically, the casting roll 90 is kept at temperature sufficient to solidify and quench the sheet 10a as it is formed, such as from about 20 to 60° C. If desired, a vacuum box may be positioned adjacent to the casting roll 90 to help keep the precursor film 10a close to the surface of the roll 90. Additionally, air knives or electrostatic pinners may help force the precursor film 10a against the surface of the casting roll 90 as it moves around a spinning roll. An air knife is a device known in the art that focuses a stream of air at a very high flow rate to pin the edges of the film.

Once cast, the film 10a may then be optionally oriented in one or more directions to further improve film uniformity and reduce thickness. Orientation may also form micropores in a film containing a filler, thus providing breathability to the film. For example, the film may be immediately reheated to a temperature below the melting point of one or more polymers in the film, but high enough to enable the composition to be drawn or stretched. In the case of sequential orientation, the "softened" film is drawn by rolls rotating at different speeds of rotation such that the sheet is stretched to the desired draw ratio in the longitudinal direction (machine direction). This "uniaxially" oriented film may then be laminated to a fibrous web. In addition, the uniaxially oriented film may also be oriented in the cross-machine direction to form a "biaxially oriented" film. For example, the film may be clamped at its lateral edges by chain clips and conveyed into a tenter oven. In the tenter oven, the film may be reheated and drawn in the cross-machine direction to the desired draw ratio by chain clips diverged in their forward travel.

Referring again to FIG. 1, for instance, one method for forming a uniaxially oriented film is shown. As illustrated, the precursor film 10a is directed to a film-orientation unit 100 or machine direction orienter ("MDO"), such as commercially available from Marshall and Willams, Co. of Providence, R.I. The MDO has a plurality of stretching rolls (such as from 5 to 8) which progressively stretch and thin the film in the machine direction, which is the direction of travel of the film through the process as shown in FIG. 1. While the MDO 100 is illustrated with eight rolls, it should be understood that the number of rolls may be higher or lower, depending on the level of stretch that is desired and the degrees of stretching between each roll. The film may be stretched in either single or multiple discrete stretching operations. It should be noted that some of the rolls in an MDO apparatus may not be operating at progressively higher speeds. If desired, some of the rolls of the MDO 100 may act as preheat rolls. If present, these first few rolls heat the film 10a above room temperature (e.g., to 125° F.). The progressively faster speeds of adjacent rolls in the MDO act to stretch the film 10a. The rate at which the stretch rolls rotate determines the amount of stretch in the film and final film weight.

The resulting film 10b may then be wound and stored on a take-up roll 60. While not shown here, various additional potential processing and/or finishing steps known in the art, such as slitting, treating, aperturing, printing graphics, or lamination of the film with other layers (e.g., nonwoven web materials), may be performed without departing from the spirit and scope of the invention.

The thickness of the resulting water-sensitive elastic film may generally vary depending upon the desired use. Nevertheless, the film thickness is typically minimized to reduce the time needed for the film to disperse in water. Thus, in most embodiments of the present invention, the water-sensitive elastic film has a thickness of about 50 micrometers or less, in some embodiments from about 1 to about 100 micrometers, in some embodiments from about 5 to about 75 micrometers, and in some embodiments, from about 10 to about 60 micrometers.

Despite having such a small thickness and good sensitivity in water, the film of the present invention is nevertheless able to retain good dry mechanical properties during use. One parameter that is indicative of the relative dry strength of the film is the ultimate tensile strength, which is equal to the peak stress obtained in a stress-strain curve. Desirably, the film of the present invention exhibits an ultimate tensile strength in the machine direction ("MD") of from about 10 to about 80 Megapascals (MPa), in some embodiments from about 15 to about 60 MPa, and in some embodiments, from about 20 to about 50 MPa, and an ultimate tensile strength in the cross-machine direction ("CD") of from about 2 to about 40 Megapascals (MPa), in some embodiments from about 4 to about 40 MPa, and in some embodiments, from about 5 to about 30 MPa. Although possessing good strength, it is also desirable that the film is not too stiff. One parameter that is indicative of the relative stiffness of the film (when dry) is Young's modulus of elasticity, which is equal to the ratio of the tensile stress to the tensile strain and is determined from the slope of a stress-strain curve. For example, the film typically exhibits a Young's modulus in the machine direction ("MD") of from about 20 to about 800 Megapascals ("MPa"), in some embodiments from about 50 to about 500 MPa, and in some embodiments, from about 100 to about 400 MPa, and a Young's modulus in the cross-machine direction ("CD") of from about 20 to about 800 Megapascals ("MPa"), in some embodiments from about 50 to about 500 MPa, and in some embodiments, from about 100 to about 400 MPa.

The film is also generally extensible in that it possesses an elongation in the machine and/or cross-machine direction of about 50% or more, in some embodiments about 100% or more, in some embodiments about 200% or more, and in some embodiments, about 300% or more. Besides being extensible, the film is also generally elastic in that is capable of recovering at least about 50% of its stretched length upon release of the stretching force. The elasticity of the film may be characterized by its "percent set", which is typically about 30% or less, in some embodiments about 15% or less, in some embodiments about 10% or less, and in some embodiments, from about 0.001 % to about 5%.

The water-sensitive elastic film of the present invention may be used in a wide variety of applications. For example, as indicated above, the film may be used in an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins, pantiliners, etc.), swim wear, baby wipes, and so forth; medical absorbent articles, such as garments, fenestration materials, underpads, bedpads, bandages, absorbent drapes, and medical wipes; food service wipers; clothing articles; and so forth. Several examples of such absorbent articles are described in U.S. Pat. No. 5,649,916 to DiPalma, et al.; U.S. Pat. No. 6,110,158 to Kielpikowski; U.S. Pat. No. 6,663,611 to Blaney, et al., which are incorporated herein in their entirety by reference thereto for all purposes. Still other suitable articles are described in U.S. Patent Application Publication No. 2004/0060112 Al to Fell et al., as well as U.S. Pat. No. 4,886,512 to Damico et al.; U.S. Pat. No. 5,558,659 to Sherrod et al.; U.S. Pat. No. 6,888,044 to Fell et al.; and U.S. Pat. No. 6,511,465 to Freiburger et al., all of which are incorporated herein in their entirety by reference thereto for all purposes. Materials and processes suitable for forming such absorbent articles are well known to those skilled in the art.

As is well known in the art, the absorbent article may be provided with adhesives (e.g., pressure-sensitive adhesives) that help removably secure the article to the crotch portion of an undergarment and/or wrap up the article for disposal. Suitable pressure-sensitive adhesives, for instance, may include acrylic adhesives, natural rubber adhesives, tackified block copolymer adhesives, polyvinyl acetate adhesives, ethylene vinyl acetate adhesives, silicone adhesives, polyurethane adhesives, thermosettable pressure-sensitive adhesives, such as epoxy acrylate or epoxy polyester pressure-sensitive adhesives, etc. Such pressure-sensitive adhesives are known in the art and are described in the Handbook of Pressure Sensitive Adhesive Technology, Satas (Donatas), 1989, $2^{nd}$ edition, Van Nostrand Reinhold. The pressure sensitive adhesives may also include additives such as cross-linking agents, fillers, gases, blowing agents, glass or polymeric microspheres, silica, calcium carbonate fibers, surfactants, and so forth. The additives are included in amounts sufficient to affect the desired properties.

The location of the adhesive on the absorbent article is not critical and may vary widely depending on the intended use of the article. For example, certain feminine hygiene products (e.g., sanitary napkins) may have wings or flaps that extend laterally from a central absorbent core and are intended to be folded around the edges of the wearer's panties in the crotch region. The flaps may be provided with an adhesive (e.g., pressure-sensitive adhesive) for affixing the flaps to the underside of the wearer's panties.

Regardless of the particular location of the adhesive, however, a release liner may be employed to cover the adhesive, thereby protecting it from dirt, drying out, and premature sticking prior to use. The release liner may contain a release coating that enhances the ability of the liner to be peeled from an adhesive. The release coating contains a release agent, such as a hydrophobic polymer. Exemplary hydrophobic polymers include, for instance, silicones (e.g., polysiloxanes, epoxy silicones, etc.), perfluoroethers, fluorocarbons, polyurethanes, and so forth. Examples of such release agents are described, for instance, in U.S. Pat. No. 6,530,910 to Pomplun, et al.; U.S. Pat. No. 5,985,396 to Kerins, et al.; and U.S. Pat. No. 5,981,012 to Pomplun. et al., which are incorporated herein in their entirety by reference thereto for all purposes. One particularly suitable release agent is an amorphous polyolefin having a melt viscosity of about 400 to about 10,000 cps at 190° C., such as made by the U.S. Rexene Company under the tradename REXTAC® (e.g., RT2315, RT2535 and RT2330). The release coating may also contain a detackifier, such as a low molecular weight, highly branched polyolefin. A particularly suitable low molecular weight, highly branched polyolefin is VYBAR® 253, which is made by the Petrolite Corporation. Other additives may also be employed in the release coating, such as compatibilizers, processing aids, plasticizers, tackifiers, slip agents, and antimicrobial agents, and so forth. The release coating may be applied to one or both surfaces of the liner, and may cover all or only a portion of a surface. Any suitable technique may be employed to apply the release coating, such as solvent-based coating, hot melt coating, solventless coating, etc. Solvent-based coatings are typically applied to the release liner by processes such as roll coating, knife coating, curtain coating, gravure coating, wound rod coating, and so forth. The solvent (e.g., water) is then removed by drying in an oven, and the coating is optionally cured in the oven. Solventless coatings may include solid compositions, such as silicones or epoxy silicones, which are coated onto the liner and then cured by exposure to ultraviolet light. Optional steps include priming the liner before coating or surface modification of the liner, such as with corona treatment. Hot melt coatings, such as polyethylenes or perfluoroethers, may be heated and then applied through a die or with a heated knife. Hot melt coatings may be applied by co-extruding the release agent with the release liner in blown film or sheet extruder for ease of coating and for process efficiency.

Figure 2:
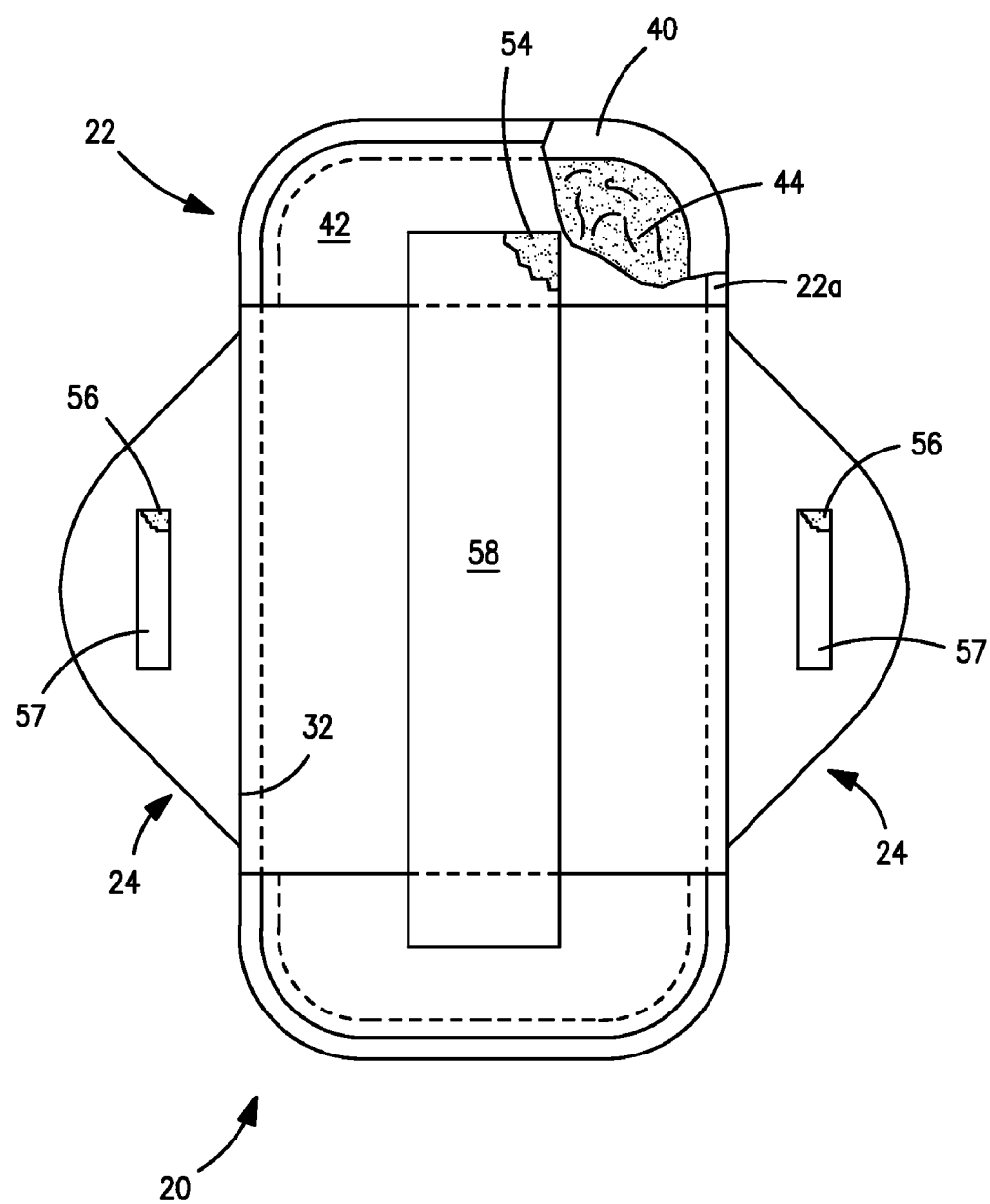
FIG. 2 is a top view of an absorbent article that may be formed in accordance with one embodiment of the present invention.

To facilitate its ability to be easily disposed, the release liner may be formed from a water-sensitive film in accordance with the present invention. In this regard, one particular embodiment of a sanitary napkin that may employ the water-sensitive film will now be described in more detail. For purposes of illustration only, an absorbent article 20 is shown in FIG. 2 as a sanitary napkin for feminine hygiene. In the illustrated embodiment, the absorbent article 20 includes a main body portion 22 containing a topsheet 40, an outer cover or backsheet 42, an absorbent core 44 positioned between the backsheet 42 and the topsheet 40, and a pair of flaps 24 extending from each longitudinal side 22*a* of the main body portion 22. The topsheet 40 defines a bodyfacing surface of the absorbent article 20. The absorbent core 44 is positioned inward from the outer periphery of the absorbent article 20 and includes a body-facing side positioned adjacent the topsheet 40 and a garment-facing surface positioned adjacent the backsheet 42.

The topsheet 40 is generally designed to contact the body of the user and is liquid-permeable. The topsheet 40 may surround the absorbent core 44 so that it completely encases the absorbent article 20. Alternatively, the topsheet 40 and the backsheet 42 may extend beyond the absorbent core 44 and be peripherally joined together, either entirely or partially, using known techniques. Typically, the topsheet 40 and the backsheet 42 are joined by adhesive bonding, ultrasonic bonding, or any other suitable joining method known in the art. The topsheet 40 is sanitary, clean in appearance, and somewhat opaque to hide bodily discharges collected in and absorbed by the absorbent core 44. The topsheet 40 further exhibits good strike-through and rewet characteristics permitting bodily discharges to rapidly penetrate through the topsheet 40 to the absorbent core 44, but not allow the body fluid to flow back through the topsheet 40 to the skin of the wearer. For example, some suitable materials that may be used for the topsheet 40 include nonwoven materials, perforated thermoplastic films, or combinations thereof. A nonwoven fabric made from polyester, polyethylene, polypropylene, bicomponent, nylon, rayon, or like fibers may be utilized. For instance, a white uniform spunbond material is particularly desirable because the color exhibits good masking properties to hide menses that has passed through it. U.S. Pat. No. 4,801,494 to Datta, et al. and U.S. Pat. No. 4,908,026 to Sukiennik et al. teach various other cover materials that may be used in the present invention.

The topsheet 40 may also contain a plurality of apertures (not shown) formed therethrough to permit body fluid to pass more readily into the absorbent core 44. The apertures may be randomly or uniformly arranged throughout the topsheet 40, or they may be located only in the narrow longitudinal band or strip arranged along the longitudinal axis X-X of the absorbent article 20. The apertures permit rapid penetration of body fluid down into the absorbent core 44. The size, shape, diameter and number of apertures may be varied to suit one's particular needs.

As stated above, the absorbent article also includes a backsheet 42. The backsheet 42 is generally liquid-impermeable and designed to face the inner surface, i.e., the crotch portion of an undergarment (not shown). The backsheet 42 may permit a passage of air or vapor out of the absorbent article 20, while still blocking the passage of liquids. Any liquid-impermeable material may generally be utilized to form the backsheet 42. For example, one suitable material that may be utilized is a microembossed polymeric film, such as polyethylene or polypropylene. In particular embodiments, a polyethylene film is utilized that has a thickness in the range of about 0.2 mils to about 5.0 mils, and particularly between about 0.5 to about 3.0 mils.

The absorbent article 20 also contains an absorbent core 44 positioned between the topsheet 40 and the backsheet 42. The absorbent core 44 may be formed from a single absorbent member or a composite containing separate and distinct absorbent members. It should be understood, however, that any number of absorbent members may be utilized in the present invention. For example, in one embodiment, the absorbent core 44 may contain an intake member (not shown) positioned between the topsheet 40 and a transfer delay member (not shown). The intake member may be made of a material that is capable of rapidly transferring, in the z-direction, body fluid that is delivered to the topsheet 40. The intake member may generally have any shape and/or size desired. In one embodiment, the intake member has a rectangular shape, with a length equal to or less than the overall length of the absorbent article 20, and a width less than the width of the absorbent article 20. For example, a length of between about 150 mm to about 300 mm and a width of between about 10 mm to about 60 mm may be utilized.

Any of a variety of different materials may be used for the intake member to accomplish the above-mentioned functions. The material may be synthetic, cellulosic, or a combination of synthetic and cellulosic materials. For example, airlaid cellulosic tissues may be suitable for use in the intake member. The airlaid cellulosic tissue may have a basis weight ranging from about 10 grams per square meter (gsm) to about 300 gsm, and in some embodiments, between about 100 gsm to about 250 gsm. In one embodiment, the airlaid cellulosic tissue has a basis weight of about 200 gsm. The airlaid tissue may be formed from hardwood and/or softwood fibers. The airlaid tissue has a fine pore structure and provides an excellent wicking capacity, especially for menses.

If desired, a transfer delay member (not shown) may be positioned vertically below the intake member. The transfer delay member may contain a material that is less hydrophilic than the other absorbent members, and may generally be characterized as being substantially hydrophobic. For example, the transfer delay member may be a nonwoven fibrous web composed of a relatively hydrophobic material, such as polypropylene, polyethylene, polyester or the like, and also may be composed of a blend of such materials. One example of a material suitable for the transfer delay member is a spunbond web composed of polypropylene, multi-lobal fibers. Further examples of suitable transfer delay member materials include spunbond webs composed of polypropylene fibers, which may be round, tri-lobal or poly-lobal in cross-sectional shape and which may be hollow or solid in structure. Typically the webs are bonded, such as by thermal bonding, over about 3% to about 30% of the web area. Other examples of suitable materials that may be used for the transfer delay member are described in U.S. Pat. No. 4,798,603 to Meyer, et al. and U.S. Pat. No. 5,248,309 to Serbiak, et al., which are incorporated herein in their entirety by reference thereto for all purposes. To adjust the performance of the invention, the transfer delay member may also be treated with a selected amount of surfactant to increase its initial wettability.

The transfer delay member may generally have any size, such as a length of about 150 mm to about 300 mm. Typically, the length of the transfer delay member is approximately equal to the length of the absorbent article 20. The transfer delay member may also be equal in width to the intake member, but is typically wider. For example, the width of the transfer delay member may be from between about 50 mm to about 75 mm, and particularly about 48 mm. The transfer delay member typically has a basis weight less than that of the other absorbent members. For example, the basis weight of the transfer delay member is typically less than about 150 grams per square meter (gsm), and in some embodiments, between about 10 gsm to about 100 gsm. In one particular embodiment, the transfer delay member is formed from a spunbonded web having a basis weight of about 30 gsm.

Besides the above-mentioned members, the absorbent core 44 may also include a composite absorbent member (not shown), such as a coform material. In this instance, fluids may be wicked from the transfer delay member into the composite absorbent member. The composite absorbent member may be formed separately from the intake member and/or transfer delay member, or may be formed simultaneously therewith. In one embodiment, for example, the composite absorbent member may be formed on the transfer delay member or intake member, which acts a carrier during the coform process described above.

Regardless of its particular construction, the absorbent article 20 typically contains an adhesive for securing to an undergarment. An adhesive may be provided at any location of the absorbent article 20, such as on the lower surface of the backsheet 42. In this particular embodiment, the backsheet 42 carries a longitudinally central strip of garment adhesive 54 covered before use by a peelable release liner 58, which may be formed in accordance with the present invention. Each of the flaps 24 may also contain an adhesive 56 positioned adjacent to the distal edge 34 of the flap 24. A peelable release liner 57, which may also be formed in accordance with the present invention, may cover the adhesive 56 before use. Thus, when a user of the sanitary absorbent article 20 wishes to expose the adhesives 54 and 56 and secure the absorbent article 20 to the underside of an undergarment, the user simply peels away the liners 57 and 58 and disposed them in a water-based disposal system (e.g., in a toilet).

Although various configurations of a release liner have been described above, it should be understood that other release liner configurations are also included within the scope of the present invention. Further, the present invention is by no means limited to release liners and the water-sensitive elastic film may be incorporated into a variety of different components of an absorbent article. For example, referring again to FIG. 2, the backsheet 42 of the napkin 20 may include the water-sensitive film of the present invention. In such embodiments, the film may be used alone to form the backsheet 42 or laminated to one or more additional materials, such as a nonwoven web. The water-sensitive elastic film of the present invention may also be used in applications other than absorbent articles. For example, the film may be employed as an individual wrap, packaging pouch, or bag for the disposal of a variety of articles, such as food products, absorbent articles, etc. Various suitable pouch, wrap, or bag configurations for absorbent articles are disclosed, for instance, in U.S. Pat. No. 6,716,203 to Sorebo, et al. and U.S. Pat. No. 6,380,445 to Moder, et al., as well as U.S. Patent Application Publication No. 2003/0116462 to Sorebo, et al., all of which are incorporated herein in their entirety by reference thereto for all purposes.

The present invention may be better understood with reference to the following examples.

Test Methods

Apparent Melt Viscosity:

The rheological properties of polymer samples were determined using a Gottfert Rheograph 2003 capillary rheometer with WinRHEO version 2.31 analysis software. The setup included a 2000-bar pressure transducer and a 30/1:0/180 roundhole capillary die. Sample loading was done by alternating between sample addition and packing with a ramrod. A 2-minute melt time preceded each test to allow the polymer to completely melt at a test temperature (150° C. or 160° C.). The capillary rheometer determined the apparent melt viscosity (Pa·s) at various shear rates, such as 100, 200, 500, 1000, 2000, and 4000 s$^{-1}$. The resultant rheology curve of apparent shear rate versus apparent melt viscosity gave an indication of how the polymer would run at that temperature in an extrusion process.

Tensile Properties:

The strip tensile strength values were determined in substantial accordance with ASTM Standard D-5034. A constant-rate-of-extension type of tensile tester was employed. The tensile testing system was a Sintech 1/D tensile tester, which is available from Sintech Corp. of Cary, N.C. The tensile tester was equipped with TESTWORKS 4.08B software from MTS Corporation to support the testing. An appropriate load cell was selected so that the tested value fell within the range of 10-90% of the full scale load. The film samples were initially cut into dog-bone shapes with a center width of 3.0 mm before testing. The samples were held between grips having a front and back face measuring 25.4 millimeters×76 millimeters. The grip faces were rubberized, and the longer dimension of the grip was perpendicular to the direction of pull. The grip pressure was pneumatically maintained at a pressure of 40 pounds per square inch. The tensile test was run using a gauge length of 18.0 millimeters and a break sensitivity of 40%. Five samples were tested by applying the test load along the machine-direction and five samples were tested by applying the test load along the cross direction. During the test, samples were stretched at a crosshead speed of abut 127 millimeters per minute until breakage occurred. The modulus, peak stress, and elongation were measured in the machine direction ("MD") and cross-machine directions ("CD").

Water Disintegration Test:

The rate of film disintegration in tap water was tested using a "slosh box", which has a physical dimension of a 14"×18"× 12" high plastic box on a hinged platform. One end of the platform is attached to the reciprocating cam. The typical amplitude is ±2" (4" range), with sloshing occurring at 0.5-1.5 sloshes per second. The preferred action is 0.9-1.3 sloshes per second. During a test, the slosh box rocks up and down with the water inside, "sloshing" back and forth. This action produces a wave front and intermittent motion on a sample susceptible to dispersing in water. To quantify a measurement of sample film disintegration in water, without image analysis, simply timing is sufficient. Three liters of tap water were added into the slosh box and resulted in ~5.5" water depth in the box. A frequency of 3.5 was selected for the testing. Each film sample was cut into 1"×3" size. Three pieces were dropped into the slosh box. The time to disintegrate the sample under the defined conditions was recorded twice for each sample. The average of the time to the sample disintegration is then reported. Generally, films reach an acceptable dispersion point when no piece is larger than 25 mm² in size within 6 hours of agitation.

Cycle Testing

The materials were tested using a cyclical testing procedure to determine percent set. In particular, 1-cycle testing was utilized to 100% defined elongation. The testing was done on a Sintech Corp. constant rate of extension tester 1/D equipped with TESTWORKS 4.08B software from MTS Corporation to support the testing. The test was conducted under ambient conditions. For this test, the sample size was 1 inches (2.54 centimeters) in the cross-machine direction by 3 inches (7.6 centimeter) in the machine direction. The grip size was 3 inches (7.6 centimeters) in width and the grip separation was 4 inches. The samples were loaded such that the machine direction of the sample was in the vertical direction. A preload of approximately 20 to 30 grams was set. The test pulled the sample to 100% elongation at a speed of 20 inches (50.8 centimeters) per minute, held the sample in an elongated state for 30 seconds, and then returned the sample to zero elongation at a speed of 20 inches (50.8 centimeters) per minute. Thereafter, the film length was immediately measured and again measured in 10, 20, and 30 minutes. The percent that did not recover ("percent set") was determined by subtracting the length of the film 30 minutes after cycle testing from the original length of the film, and then dividing this number by the original length of the film.

EXAMPLE 1

A blend was formed 42 wt. % of a water-soluble polymer, 30 wt. % of an elastomer, and 18 wt. % of plasticizer. The water-soluble polymer was CELVOL™ 523S (polyvinyl alcohol, Celanese). The elastomer was ESTANE™ 58245, an aromatic, polyether-based thermoplastic polyurethane available from Lubrizol. The plasticizer was glycerin (Cognis Corporation, Cincinnati, Ohio). These components were fed into a co-rotating twin screw extruder (ZSK-30, Werner and Pfleiderer Corporation, Ramsey, N.J.). In addition, 10 wt. % calcium carbonate (2sst CaCO₃ from Omya, Alpharetta, Ga.) was fed through the side ⅔ of distance away from the first zone. The extruder diameter was 30 mm and the length of the screws was up to 1328 mm. The extruder has 14 barrels, numbered consecutively 1 to 14 from the feed hopper to the die. The temperature profile of zones 1 to 14 of the extruder was 110° C., 130° C., 190° C., 190° C., 190° C., 180° C., and 170° C., respectively. The screw speed was set at 150 rpm to achieve a torque of between 45-50%, $P_{melt}$ of 130-200 psi, and an output of about 18 to 20 lb/hr. The resulting film exhibited flow lines, which generally indicated that the materials were incompatible. The film had a thickness of about 0.002 inches.

EXAMPLE 2

A blend was formed 42 wt. % of a water-soluble polymer, 30 wt. % of an elastomer, and 18 wt. % of plasticizer. The water-soluble polymer was CELVOL™ 523S (polyvinyl alcohol, Celanese). The elastomer was ESTANE™ 58245, an aromatic, polyether-based thermoplastic polyurethane available from Lubrizol. The plasticizer was glycerin (Cognis Corporation, Cincinnati, Ohio). These components were fed into a co-rotating twin screw extruder (ZSK-30, Werner and Pfleiderer Corporation, Ramsey, N.J.). In addition, 10 wt. % wt. % MP 30-36 talc (Barrefts Minerals, Dillon, Mont.) was fed through the side two-thirds of the total distance from the first zone. The extruder diameter was 30 mm and the length of the screws was up to 1328 mm. The extruder has 14 barrels, numbered consecutively 1 to 14 from the feed hopper to the die. The temperature profile of zones 1 to 14 of the extruder was 110° C., 130° C., 190° C., 190° C., 190° C., 180° C., and 170° C., respectively. The screw speed was set at 150 rpm to achieve a torque of between 45-50%, $P_{melt}$ of 130-200 psi, and an output of about 18 to 20 lb/hr. The strand skin was rough and showed incompatibility. No films were made from the blend.

EXAMPLE 3

A blend was formed 42 wt. % of a water-soluble polymer, 40 wt. % of an elastomer, and 18 wt. % of a plasticizer. The water-soluble polymer was ELVANOL™ 51-05 (polyvinyl alcohol, DuPont). The elastomer was ESTANE™ 58245, an aromatic, polyether-based thermoplastic polyurethane available from Lubrizol. The plasticizer was sorbitol (Glenn Corporation, White Bear Lake, Minn.). The resulting film was rigid and had a thickness of about 0.005 inches.

EXAMPLE 4

A blend was formed 50 wt. % of a water-soluble polymer, 20 wt. % of an elastomer, 15 wt. % of a plasticizer, 10 wt. % MP 30-36 (talc), and 5 wt. % of FUSABOND™ MC 190D (compatibilizer). The water-soluble polymer was CELVOL™ 523S (polyvinyl alcohol, Celanese). The elastomer was ESTANE™ 58245, an aromatic, polyether-based thermoplastic polyurethane available from Lubrizol. The plasticizer was glycerin (Cognis Corporation, Cincinnati, Ohio). The strand improved during compounding, but no film was formed.

EXAMPLE 5

A blend was formed 55 wt. % of a water-soluble polymer, 25 wt. % of an elastomer, and 20 wt. % of a plasticizer. The water-soluble polymer was CELVOL™ 523S (polyvinyl alcohol, Celanese). The elastomer was DESMOPAN™ DP 9370A, a polyether-based thermoplastic polyurethane from Bayer Material Science of Pittsburgh, Pa. The plasticizer used was glycerin (Cognis Corporation, Cincinnati, Ohio). With these materials, pellets were made from the compounding process. However, the pellets did not have the processability required to make a film.

EXAMPLE 6

A blend was formed 60 wt. % of a water-soluble polymer, 25 wt. % of an elastomer, and 15 wt. % of a plasticizer. The water-soluble polymer was CELVOL™ 513 (polyvinyl alcohol, Celanese). The elastomer was DESMOPAN™ DP 9370A, a polyether-based thermoplastic polyurethane from Bayer Material Science of Pittsburgh, Pa. The plasticizer was glycerin (Cognis Corporation, Cincinnati, Ohio). With these materials, pellets were obtained during compounding, although no film was formed.

EXAMPLE 7

A plasticized PVOH was formed from ELVANOL™ 51-05 (DuPont), which was obtained by feeding 85 wt. % PVOH powder into a co-rotating twin screw extruder (ZSK-30, Werner and Pfleiderer Corporation, Ramsey, N.J.). Glycerin (Cognis Corporation, Cincinnati, Ohio) was used as a plasticizer that was fed at 15 wt % into the zone 1 by an Eldex pump. The extruder diameter was 30 mm and the length of the screws was up to 1328 mm. The extruder has 14 barrels, numbered consecutively 1 to 14 from the feed hopper to the die. The temperature profile of zones 1 to 14 of the extruder was 95° C., 145° C., 185° C., 185° C., 175° C., 160 and 155° C., respectively. The screw speed was set at 150 rpm to achieve a torque of between 50~55%, Pmeit of 180~190 psi, and an output of about 19 lb/hr.

EXAMPLES 8-9

The plasticized PVOH from Example 7 was used to blend with DESMOPAN™ DP 9370A (Bayer Material Science of Pittsburgh, Pa.) to create a water responsive resin. More specifically, plasticized PVOH from Example 7 (feeding rate: 12 lbs/hr) and DESMOPAN™ DP 9370A (feeding rate: 8 lbs/hr) were respectively fed into a co-rotating twin screw extruder (ZSK-30, Werner and Pfleiderer Corporation, Ramsey, N.J.). Two gravimetric K-Tron feeders were used (K-Tron America, Inc., Pitman, N.J.). The vent at the end of the extruder was open to release some moisture. A 3-hole die of 3 mm diameter that is separated by 10 mm space was used to shape the melt into strands that were cooled on a conveyer belt and then pelletized. The temperature profile of zones 1 to 14 of the extruder was 140° C., 160° C., 170° C., 180° C., 180° C., 170° C., and 160° C., respectively. The other conditions used to plasticize the ELVANOL™ 51-05 (Example 7) and to compound the plasticized polymer with DESMOPAN™ DP 9370A (Examples 8-9) are set forth below in Table 1.

TABLE 1

| | | Processing Conditions | | | | | |
|---|---|---|---|---|---|---|---|
| Ex. | Total Material Feed Rate (lb/hr) | Desmopan DP 9370A (wt. %) | Elvanol 51-05 (wt. %) | Glycerin (wt. %) | Extruder Speed (rpm) | Pmelt (psi) | Torque (%) | Melt temperature (° C.) |
| 7 | 19 | — | 85.0 | 15.0 | 150 | 180-190 | 50-55 | 198 |
| 8 | 20 | 40 | 51.0 | 9.0 | 150 | 190-240 | 66-71 | 164 |
| 9 | 20 | 30 | 59.5 | 10.5 | 150 | 230-260 | 72-80 | 164 |

The strands from these blends were smooth, which generally indicated good resin compatibility. The blends of Examples 8-9 were then provided to a HAAKE Rheomex 252 single screw extruder for film casting. The screw speed was set at 45 to 55 rpm and the temperature profile of the extruder from zone 1 to 5 was 200° C., 200° C., 205° C., 197° C., and 187° C.,respectively. The melt temperature was 204° C. to 209° C., the torque was 1500 to 2000 m-g, and the die pressure was 1100 to 1500 psi. The resulting films had a thickness of about 0.002 inches (~50.8 micrometers). In some cases, a release paper was introduced to the first chill roll.

EXAMPLE 10

A film was formed from the blend of Example 7 as described above.

EXAMPLE 11

The mechanical properties of the films of Examples 8-10 were tested as described above. The results are shown in Table 2.

TABLE 2

| | | Thermoplastic Film Mechanical Tensile Properties | | | | | | | |
|---|---|---|---|---|---|---|---|---|---|
| | | | Film Thickness | | Peak Stress (MPa) | | Elongation (%) | | Modulus (MPa) | |
| Example | Sample Description | Composition | MD (mil) | CD (mil) | MD | CD | MD | CD | MD | CD |
| 8 | p-Elvanol/Desmopan | 60/40 | 2.2 | 2.1 | 26 | 21 | 368 | 349 | 74 | 74 |
| 9 | p-Elvanol/Desmopan | 70/30 | 2.2 | 2.0 | 37 | 25 | 317 | 280 | 216 | 147 |
| 10 | p-Elvanol (Elvanol 51-05/Glycerin) | 85/15 | 1.1 | 1.0 | 48 | 46 | 173 | 161 | 1224 | 1554 |

The modulus of the film of Example 8 was low, indicating that it was flexible and soft. The plasticized ELVANOL™ 51-05 film of Example 10 showed the highest modulus and peak stress, indicating a rigid film. With the presence of an elastomer in the blends (Examples 8 and 9), the film elongation was generally greater than that for the plasticized ELVANOL™ 51-05.

EXAMPLE 12

The films of Examples 8-10 were subjected to the above-described water disintegration test. The results are set forth below in Table 3.

TABLE 3

| | | | | To First Break | | To 25 mm2 pieces | |
|---|---|---|---|---|---|---|---|
| | | Water Temp. | | | | | |
| | Run | (° C.) | RPM | (min.) | (sec.) | (min.) | (sec.) |
| Example 8 | | | | | | | |
| p-Elvanol/Desmopan (60/40) | 1 | 23.6 | 26 | 1 | 5.00 | 4 | 16.00 |
| | 2 | 23.6 | 26 | 0 | 58.00 | 3 | 34.00 |
| Example 9 | | | | | | | |
| p-Elvanol/Desmopan (70/30) | 1 | 23.6 | 26 | 0 | 33.00 | 0 | 55.00 |
| | 2 | 23.6 | 26 | 0 | 35.00 | 0 | 58.00 |
| Example 10 | | | | | | | |
| p-Elvanol | 1 | 23.6 | 26 | 0 | 13.00 | 0 | 40.00 |
| | 2 | 23.6 | 26 | 0 | 7.00 | 0 | 25.00 |

Film Disintegration Time; Time (min.)

As indicated, the film of Example 8 began to disperse after about 1 minute and broke into two pieces in just over 3 to 4 minutes. As the elastomer content decreased to 30% in Example 9, the time needed for the film to disperse was less than one minute, which was comparable to the plasticized ELVANOL™ 51-05 film of Example 10. In general, once the samples were placed in water, they started to change color.

EXAMPLE 13

To assess elasticity, the films of Examples 8-10 were subjected to cycle testing as described above. Before testing, the net gauge film length was 51 millimeters. The results are set forth below in Table 4.

EXAMPLE 14

Figure 3:
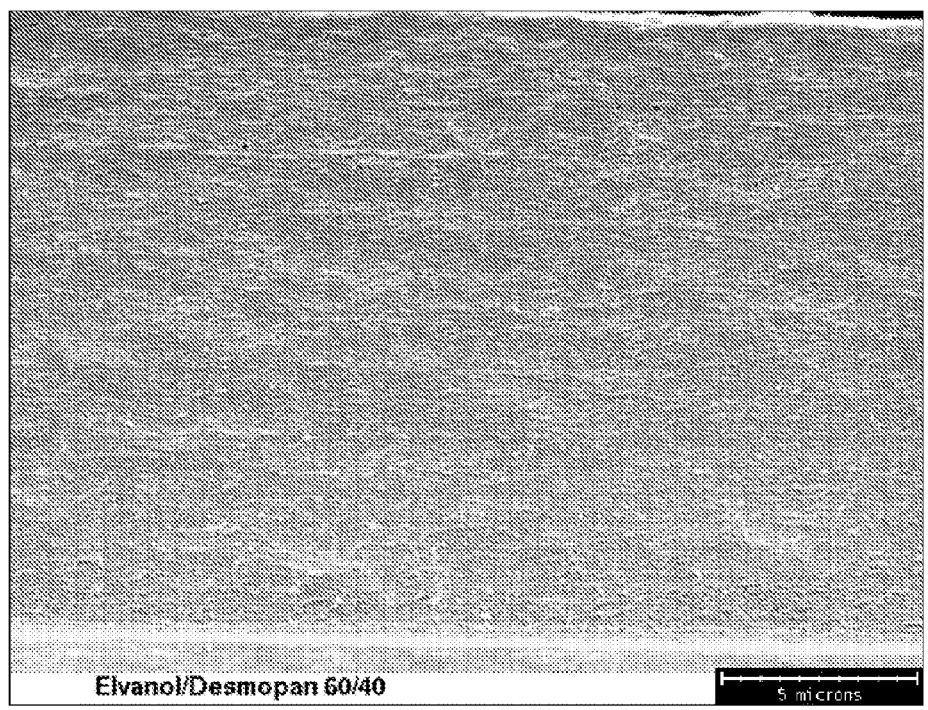
FIG. 3 is an SEM photograph of the film of Example 8.

A scanning electron microscopy (SEM) photograph was taken of the film of Example 8. The photograph was obtained by plasma etching/optical method using the standard secondary electron imaging mode achieved by a positive-biased Everhart-Thornley detector. The results are shown in FIG. 3. As indicated, the film of Example 8 exhibited a substantially continuous phase with a finely distributed elastomer phase showing good compatibility between PVOH and polyurethane, which can be easily accessed by water to induce disintegration.

EXAMPLE 15

Figure 4:
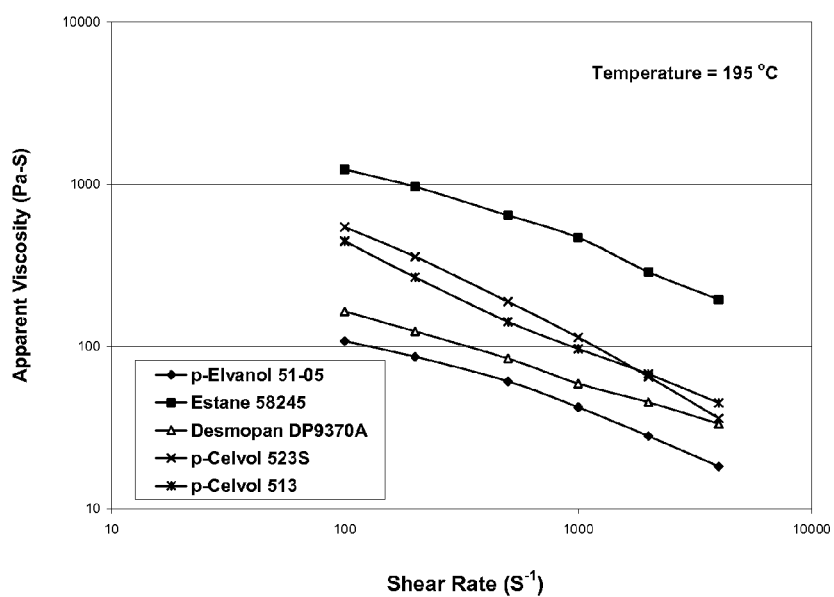
FIG. 4 is a graph showing the melt viscosity of plasticized ELVANOL™ 51-05 (a polyvinyl alcohol), CELVOL™ 523S (a polyvinyl alcohol), CELVOL™ 513 (a polyvinyl alcohol), DESMOPAN™ DP9370A (a polyester-based thermoplastic polyurethane), and ESTANE™ 58245 (an aromatic, polyether-based thermoplastic polyurethane) at various shear rates.

The melt viscosity was determined for plasticized Elvanol™ 51-05, Celvol™ 523S, Celvol™ 513, Desmopan™ DP9370A, and Estane™ 58245 using a Gottfert Rhoegraph 2003 capillary rheometer. The results are shown in FIG. 4. For comparative purposes, a shear rate of $1000\ s^{-1}$ was also selected to calculate ratios of the plasticized PVOH or starch-based blend to Estane™]58245 or Desmopan™ DP9370A, respectively. These values are tabulated in Table 5.

TABLE 4

Film Mechanical Stretch and Recovery Testing

| Example | Sample Description | Original | After Test | After 10 min | After 20 min | After 30 min | % Not Recovered |
|---|---|---|---|---|---|---|---|
| 8 | p-Elvanol/Desmopan (60/40) - MD | 51 | 58 | 54 | 53 | 53 | 3.9 |
| | p-Elvanol/Desmopan (60/40) - CD | 51 | 57 | 52 | 51 | 51 | 0.0 |
| 9 | p-Elvanol/Desmopan (70/30) - MD | 51 | 71 | 55 | 53 | 53 | 3.9 |
| | p-Elvanol/Desmopan (70/30) - CD | 51 | 69 | 55 | 54 | 53 | 3.9 |
| 10 | p-Elvanol (100%) - MD | 51 | 97 | 85 | 84 | 84 | 64.7 |
| | p-Elvanol (100%) - CD | 51 | N/A | N/A | N/A | N/A | N/A |

TABLE 5

The Ratio of Plasticized PVOH to Thermoplastic Polyurethanes

| Shear Rate (s$^{-1}$) | Apparent Viscosity (Pa-S) | | | | |
|---|---|---|---|---|---|
| | p-Celvol 513 | p-Celvol 523S | p-Elvanol 51-05 | Estane 58245 | Desmpopan DP9370A |
| 1000 | 97 | 114 | 42 | 470 | 59 |
| | Examples 1, 2, and 3 | Example 5 | Example 6 | Example 8 | Example 9 |
| Viscosity Ratio | <0.2 | 1.9 | 1.6 | 0.7 | 0.7 |

The preferred ratio for generating water-sensitive films was from 0.5 to 1.5.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. An absorbent article that comprises a body portion that includes a liquid permeable topsheet, generally liquid impermeable backsheet, absorbent core positioned between the backsheet and the topsheet, and optionally a release liner coated with a release agent, wherein the backsheet, the release liner or both comprise water-sensitive elastic film comprising:
   at least one water-soluble polymer, wherein the water-soluble polymer has a weight average molecular weight of from about 10,000 to about 150,000 grams per mole and a number average molecular weight of from about 1,000 to about 80,000 grams per mole;
   at least one plasticizer, wherein the weight ratio of the water-soluble polymer to the plasticizer is from about 1 to about 50; and
   at least one thermoplastic polyurethane synthesized from at least one polyol and at least one organic diisocyanate, wherein the weight ratio of the water-soluble polymer to the thermoplastic polyurethane is from about 0.1 to about 2.5.

2. The absorbent article of claim 1, wherein the water-soluble polymer includes vinyl pyrrolidone, hydroxyethyl acrylate or methacrylate, hydroxypropyl acrylate or methacrylate, acrylic or methacrylic acid, acrylic or methacrylic esters or vinyl pyridine, acrylamide, vinyl acetate, vinyl alcohol, ethylene oxide, or a combination thereof.

3. The absorbent article of claim 1, wherein the water-soluble polymer includes a vinyl alcohol polymer.

4. The absorbent article of claim 3, wherein the vinyl alcohol polymer has a degree of hydrolysis of from about 80 mole % to about 90 mole %.

5. The absorbent article of claim 1, wherein the water-soluble polymer has a weight average molecular weight of from about 30,000 to about 75,000 grams per mole and a number average molecular weight of from about 10,000 to about 40,000 grams per mole.

6. The absorbent article of claim 1, wherein the water-soluble polymer has a solution viscosity of from about 50 to about 800 milliPascal seconds, as determined in a 4% aqueous solution at 20° C.

7. The absorbent article of claim 1, wherein the water-soluble polymer has a solution viscosity of from about 200 to about 600 milliPascal seconds, as determined in a 4% aqueous solution at 20° C.

8. The absorbent article of claim 1, wherein the ratio of the melt viscosity of the thermoplastic polyurethane to the plasticized water-soluble polymer is from about 0.5 to about 1.5.

9. The absorbent article of claim 1, wherein the plasticizer includes a polyhydric alcohol.

10. The absorbent article of claim 9, wherein the polyhydric alcohol includes a sugar alcohol.

11. The absorbent article of claim 1, wherein the weight ratio of the water-soluble polymer to the plasticizer is from about 3 to about 15.

12. The absorbent article of claim 1, wherein the plasticizer constitutes from about 1 wt. % to about 30 wt. % of the film and the water-soluble polymer constitutes from about 20 wt. % to about 90 wt. % of the film.

13. The absorbent article of claim 1, wherein the polyol includes a polyether polyol and the organic diisocyanate includes an aromatic diisocyanate.

14. The absorbent article of claim 1, wherein the thermoplastic polyurethane has a melting point of from about 75° C. to about 250° C. and a glass transition temperature of from about −150° C. to about 0° C.

15. The absorbent article of claim 1, wherein the weight ratio of the water-soluble polymer to the thermoplastic polyurethane is from about 1.0 to about 2.0.

16. The absorbent article of claim 1, wherein the thermoplastic polyurethane constitutes from about 10 wt. % to about 70 wt. % of the film.

17. The absorbent article of claim 1, wherein the thermoplastic polyurethane constitutes from about 20 wt. % to about 50 wt. % of the film.

18. The absorbent article of claim 1, wherein the film has an elongation of about 100% or more in the machine direction, cross-machine direction, or both.

19. The absorbent article of claim 1, wherein the film has a percent set of about 30% or less.

20. The absorbent article of claim 1, wherein the film has a percent set of about 10% or less.

21. The absorbent article of claim 1, wherein the backsheet includes the water-sensitive elastic film.

22. The absorbent article of claim 1, wherein the release liner includes the water-sensitive elastic film.

* * * * *